US007126682B2

(12) United States Patent
Rowe et al.

(10) Patent No.: US 7,126,682 B2
(45) Date of Patent: Oct. 24, 2006

(54) ENCODED VARIABLE FILTER SPECTROMETER

(75) Inventors: Robert K. Rowe, Corrales, NM (US); Russell E. Abbink, Albuquerque, NM (US); Stephan P. Corcoran, Corrales, NM (US)

(73) Assignee: Rio Grande Medical Technologies, Inc., Albuquerque, NM (US)

( * ) Notice: Subject to any disclaimer, the term of this patent is extended or adjusted under 35 U.S.C. 154(b) by 334 days.

(21) Appl. No.: 09/832,631

(22) Filed: Apr. 11, 2001

(65) Prior Publication Data

US 2002/0171834 A1    Nov. 21, 2002

(51) Int. Cl.
*G01J 3/04*    (2006.01)

(52) U.S. Cl. ............... 356/310; 356/326; 356/330; 250/339.07

(58) Field of Classification Search ............ 356/418, 356/310, 328, 326, 330, 51; 250/339.07; 359/291, 292; 209/579; 385/12, 31, 39
See application file for complete search history.

(56) References Cited

U.S. PATENT DOCUMENTS

| | | | |
|---|---|---|---|
| 3,910,701 A | | 10/1975 | Henderson et al. |
| 3,929,398 A | * | 12/1975 | Bates .................. 356/416 |
| 3,950,101 A | * | 4/1976 | Dewey, Jr. ............. 356/51 |
| 4,035,083 A | | 7/1977 | Woodriff et al. |
| 4,142,797 A | | 3/1979 | Astheimer |
| 4,169,676 A | | 10/1979 | Kaiser |
| 4,260,220 A | | 4/1981 | Whitehead |
| 4,319,830 A | | 3/1982 | Roach |
| 4,427,889 A | | 1/1984 | Muller |
| 4,537,484 A | | 8/1985 | Fowler |
| 4,598,715 A | | 7/1986 | Machler et al. |
| 4,653,880 A | | 3/1987 | Sting et al. |
| 4,654,530 A | | 3/1987 | Dybwad |
| 4,655,225 A | | 4/1987 | Dahne et al. |
| 4,656,562 A | | 4/1987 | Sugino |
| 4,657,397 A | | 4/1987 | Oehler et al. |
| 4,661,706 A | | 4/1987 | Messerschmidt et al. |

(Continued)

FOREIGN PATENT DOCUMENTS

EP    0 426 358 B1    5/1991

(Continued)

OTHER PUBLICATIONS

Kashyap, Raman, "Theory of Fiber Bragg Gratings," Academic Press (1999) pp. 119-193.

(Continued)

*Primary Examiner*—Thong Nguyen
*Assistant Examiner*—Arnel C. Lavarias
(74) *Attorney, Agent, or Firm*—Crompton, Seager & Tufte, LLC

(57) ABSTRACT

Spectroscopic system and spectrometers including an optical bandpass filter unit having a plurality of bandpass regions and a spatial encoding unit for encoding discrete frequencies of light passing through the optical filter. The incorporation of the encoding unit allows the spectrometer system to use a detector having one or a small number of elements, rather than using a more expensive detector array typically used with filter-based spectrometers. The system can also include an integrating chamber that collects the light that is not transmitted through the bandpass filter unit, and redirects this light to strike the filter unit again, resulting in a significant increase in the optical power passing through the filter. The integrating chamber maximizes the return of the reflected light to the filter assembly and minimizes optical losses. The integrating chamber may be an orthogonal design to preserve the optical geometric characteristics of the light entering the chamber.

53 Claims, 13 Drawing Sheets

U.S. PATENT DOCUMENTS

| | | |
|---|---|---|
| 4,684,255 A | 8/1987 | Ford |
| 4,712,912 A | 12/1987 | Messerschmidt |
| 4,730,882 A | 3/1988 | Messerschmidt |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,051,901 A | 9/1991 | Endo |
| 5,068,536 A | 11/1991 | Rosenthal |
| 5,070,874 A | 12/1991 | Barnes et al. |
| 5,158,082 A | 10/1992 | Jones |
| 5,178,142 A | 1/1993 | Harjunmaa et al. |
| 5,179,951 A | 1/1993 | Knudson |
| 5,204,532 A | 4/1993 | Rosenthal |
| 5,218,660 A | 6/1993 | Omata |
| 5,222,496 A | 6/1993 | Clarke et al. |
| 5,223,715 A | 6/1993 | Taylor |
| 5,225,678 A | 7/1993 | Messerschmidt |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,291,560 A | 3/1994 | Daugman |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,355,880 A | 10/1994 | Thomas et al. |
| 5,360,004 A | 11/1994 | Purdy et al. |
| 5,361,758 A | 11/1994 | Hall et al. |
| 5,372,135 A | 12/1994 | Mendelson et al. |
| 5,379,764 A | 1/1995 | Barnes et al. |
| 5,402,778 A | 4/1995 | Chance |
| 5,419,321 A | 5/1995 | Evans |
| 5,422,483 A * | 6/1995 | Ando et al. ............ 250/339.02 |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,504,575 A * | 4/1996 | Stafford ...................... 356/330 |
| 5,515,847 A | 5/1996 | Braig et al. |
| 5,523,054 A | 6/1996 | Switalski et al. |
| 5,526,120 A | 6/1996 | Jina et al. |
| 5,533,509 A | 7/1996 | Koashi et al. |
| 5,537,208 A | 7/1996 | Bertram et al. |
| 5,552,997 A | 9/1996 | Massart |
| 5,596,992 A | 1/1997 | Haaland et al. |
| 5,606,164 A | 2/1997 | Price et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,708,593 A | 1/1998 | Saby et al. |
| 5,719,950 A | 2/1998 | Osten et al. |
| 5,724,268 A | 3/1998 | Sodickson et al. |
| 5,743,262 A | 4/1998 | Lepper, Jr. et al. |
| 5,747,806 A | 5/1998 | Khalil |
| 5,750,994 A | 5/1998 | Schlager |
| 5,782,755 A | 7/1998 | Chance et al. |
| 5,784,507 A * | 7/1998 | Holm-Kennedy et al. .... 385/31 |
| 5,792,050 A | 8/1998 | Alam et al. |
| 5,792,053 A | 8/1998 | Skladner et al. |
| 5,792,668 A | 8/1998 | Fuller et al. |
| 5,793,881 A | 8/1998 | Stiver et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,835,645 A * | 11/1998 | Jorgenson et al. ............ 385/12 |
| 5,850,623 A | 12/1998 | Carman, Jr. et al. |
| 5,853,370 A | 12/1998 | Chance et al. |
| 5,860,421 A | 1/1999 | Eppstein et al. |
| 5,870,188 A * | 2/1999 | Ozaki et al. ................. 356/301 |
| 5,886,347 A | 3/1999 | Inoue et al. |
| 5,902,033 A | 5/1999 | Levis et al. |
| 5,914,780 A | 6/1999 | Turner et al. |
| 5,923,036 A * | 7/1999 | Tague et al. ........... 250/339.07 |
| 5,933,792 A | 8/1999 | Andersen et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A | 3/2000 | Hsu et al. |
| 6,043,492 A | 3/2000 | Lee et al. |
| 6,044,285 A | 3/2000 | Chaiken et al. |
| 6,045,502 A | 4/2000 | Eppstein et al. |
| 6,046,808 A | 4/2000 | Fately |
| 6,049,727 A | 4/2000 | Crothall |
| 6,056,738 A | 5/2000 | Marchitto et al. |
| 6,057,925 A | 5/2000 | Anthon |
| 6,058,352 A | 5/2000 | Lu et al. |
| 6,061,581 A | 5/2000 | Alam et al. |
| 6,061,582 A | 5/2000 | Small et al. |
| 6,066,847 A | 5/2000 | Rosenthal |
| 6,070,093 A | 5/2000 | Oosta et al. |
| 6,073,037 A | 6/2000 | Alam et al. |
| 6,088,605 A | 7/2000 | Griffith et al. |
| 6,100,811 A | 8/2000 | Hsu et al. |
| 6,115,673 A | 9/2000 | Malin et al. |
| 6,141,101 A | 10/2000 | Bleier et al. |
| 6,147,749 A | 11/2000 | Kubo et al. |
| 6,152,876 A | 11/2000 | Robinson et al. |
| 6,157,041 A | 12/2000 | Thomas et al. |
| 6,175,407 B1 | 1/2001 | Sartor |
| 6,191,860 B1 | 2/2001 | Klinger et al. |
| 6,192,261 B1 | 2/2001 | Gratton et al. |
| 6,212,424 B1 | 4/2001 | Robinson |
| 6,226,541 B1 | 5/2001 | Eppstein et al. |
| 6,230,034 B1 | 5/2001 | Messerschmidt et al. |
| 6,236,047 B1 | 5/2001 | Malin et al. |
| 6,236,459 B1 | 5/2001 | Negahdaripour et al. |
| 6,240,306 B1 | 5/2001 | Rohrscheib et al. |
| 6,241,663 B1 | 6/2001 | Wu et al. |
| 6,571,118 B1 * | 5/2003 | Utzinger et al. ............ 600/476 |

| | | |
|---|---|---|
| 2003/0034281 A1 * | 2/2003 | Kumar .................... 209/579 |

FOREIGN PATENT DOCUMENTS

| | | |
|---|---|---|
| EP | 0 449 335 A2 | 10/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |
| EP | 0 801 297 A1 | 10/1997 |
| EP | 0 836 083 A1 | 4/1998 |
| EP | 0 843 986 A2 | 5/1998 |
| EP | 0 869 348 A2 | 10/1998 |
| EP | 0 897 691 A2 | 2/1999 |
| EP | 0 317 121 B1 | 5/1999 |
| EP | 0 982 583 A1 | 3/2000 |
| EP | 0 990 945 A1 | 4/2000 |
| JP | 2000-131143 | 5/2000 |
| JP | 2001-21489 | 1/2001 |
| WO | WO 92/00513 | 1/1992 |
| WO | WO 92/17765 | 10/1992 |
| WO | WO 93/00855 | 1/1993 |
| WO | WO 93/07801 | 4/1993 |
| WO | WO 95/22046 | 8/1995 |
| WO | WO 97/23159 | 7/1997 |
| WO | WO 97/27800 | 8/1997 |
| WO | WO 97/28437 | 8/1997 |
| WO | WO 97/28438 | 8/1997 |
| WO | WO 98/01071 | 1/1998 |
| WO | WO 98/37805 | 9/1998 |
| WO | WO 98/40723 | 9/1998 |
| WO | WO 99/09395 | 2/1999 |
| WO | WO 99/37203 | 7/1999 |
| WO | WO 99/43255 | 9/1999 |
| WO | WO 99/46731 | 9/1999 |
| WO | WO 99/55222 | 11/1999 |
| WO | WO 99/56616 | 11/1999 |
| WO | WO 01/15596 | 3/2001 |

OTHER PUBLICATIONS

U.S. Appl. No. 09/415,594, filed Oct. 8, 1999, Rowe et al.
U.S. Appl. No. 09/832,608, filed Apr. 11, 2001, Gardner et al.
U.S. Appl. No. 09/832,585, filed Apr. 11, 2001, Abbink et al.
U.S. Appl. No. 09/832,586, filed Apr. 11, 2001, Johnson.
Anderson, C. E. et al., "Fundamentals of Calibration Transfer Through Procrustes Analysis," *Appln. Spectros.*, vol. 53, No. 10 (1999) p. 1268.
Ashbourn, Julian, *Biometrics; Advanced Identity Verification*, Springer, 2000, pp. 63-4).
Bantle, John P. et al., "Glucose Measurement in Patients with Diabetes Mellitus with Dermal Interstitial Fluid," Copyright © 1997 by Mosby-Year Book, Inc., 9 pages.
Blank, T.B. et al., "Transfer of Near-Infrared Multivariate Calibrations Without Standards," *Anal. Chem.*, vol. 68 (1996) p. 2987.
Brasunas John C. et al., "Uniform Time-Sampling Fourier Transform Spectroscopy," *Applied Optics*, vol. 36, No. 10, Apr. 1, 1997, pp. 2206-2210.
Brault, James W., "New Approach to High-Precision Fourier Transform Spectrometer Design," *Applied Optics*, Vo. 35, No. 16, Jun. 1, 1996, pp. 2891-2896.
Cassarly, W.J. et al., "Distributed Lighting Systems: Uniform Light Delivery," *Source Unknown*, pp. 1698-1702.
Chang, Chong-Min et al., "An Uniform Rectangular Illuminating Optical System for Liquid Crystal Light Valve Projectors," *Euro Display '96* (1996) pp. 257-260.
Coyne, Lawrence J. et al., "Distributive Fiber Optic couplers Using Rectangular Lightguides as Mixing Elements," (Information Gatekeepers, Inc. Brookline, MA, 1979) pp. 160-164.
de Noord, Onno E., "Multivariate Calibration Standardization," *Chemometrics and Intelligent Laboratory Systems 25*, (1994) pp. 85-97.

Despain, Alvin M. et al., "A Large-Aperture Field-Widened Interferometer-Spectrometer for Airglow Studies," Aspen International Conference on Fourier Spectroscopy, 1970, pp. 293-300.
Faber, Nicolaas, "Multivariate Sensitivity for the Interpretation of the Effect of Spectral Pretreatment Methods on Near-Infrared Calibration Model Predictions," *Analytical Chemistry*, vol. 71, No. 3, Feb. 1, 1999, pp. 557-565.
Geladi, Paul et al., A Multivariate NIR Study of Skin Alterations in Diabetic Patients as Compared to Control Subjects, *J. Nera Infrared Spectrosc.*, vol. 8 (2000) pp. 217-227.
Haaland, David M. et al. "Reagentless Near-Infrared Determination of Glucose in Whole Blood Using Multivariate Calibration," *Applied Spectroscopy*, vol. 46, No. 10 (1992) pp. 1575-1578.
Harwit, M. et al., "Chapter 5—Instrumental Considerations" *Hadamard Transform Optics*, Academic Press (1979) pp. 109-145.
Heise H. Michael et al., "Near-Infrared Reflectance Spectroscopy for Noninvasive Monitoring of Metabolites," *Clin. Chem. Lab. Med. 2000*, 38(2) (2000) pp. 137-145.
Heise, H.M. et al., "Near Infrared Spectrometric Investigation of Pulsatile Blood Flow for Non-Invasive Metabolite Monitoring," *CP430, Fourier Transform Spectroscopy: 11th International Conference*, (1998) pp. 282-285.
Heise, H.M. et al., "Noninvasive Blood Glucose Sensors Based on Near-Infrared Spectroscopy," *Artif Organs*, vol. 18, No. 6 (1994) pp. 1-9.
Heise, H.M. "Non-Invasive Monitoring of Metabolites Using Near Infrared Spectroscopy: State of the Art," *Horm. Metab. Res.*, vol. 28 (1996) pp. 527-534.
Hopkins, George W. et al., "In-vivo NIR Diffuse-reflectance Tissue Spectroscopy of Human Subjects," *SPIE*, vol. 3597, Jan. 1999, pp. 632-641.
Jagemann, Kay-Uwe et al. "Application of Near-Infrared Spectroscopy for Non-Invasive Determination of Blood/Tissue Glucose Using Neural Networks," *Zeitschrift for Physikalische Chemie*, Bd. 191, S. 179-190 (1995).
Khalil, Omar S, "Spectroscopic and Clinical Aspects of Noninvasive Glucose Measurements," *Clinical Chemistry*, 45:2 (1999) pp. 165-177.
Kohl, Matthias et al., "The Influence of Glucose Concentration Upon the Transport of Light in Tissue-simulating Phantoms," *Phys. Med. Biol.*, vol. 40 (1995) pp. 1267-1287.
Korte, E.H. et al., "Infrared Diffuse Reflectance Accessory for Local Analysis on Bulky Samples," *Applied Spectroscopy*, vol. 42, No. 1, Jan. 1988, pp. 38-43.
Kumar, G. et al., "Optimal Probe Geometry for Near-Infrared Spectroscopy of Biological Tissue," *Applied Spectroscopy*, vol. 36 (1997) p. 2286.
Lorber, Avraham et al., "Local Centering in Multivariate Calibration," *Journal of Chemometrics*, vol. 10 (1996) pp. 215-220.
Lorber, Avraham et al., "Net Analyte Signal Calculation in Multivariate Calibration," *Analytical Chemistry*, vol. 69, No. 8, Apr. 15, 1997, pp. 1620-1626.
Marbach, Ralf, "Measurement Techniques for IR Spectroscopic Blood Glucose Determination," (1994) pp. 1-158.
Marbach, R. et al. "Noninvasive Blood Glucose Assay by Near-Infrared Diffuse Reflectance Spectroscopy of the Human Inner Lip," *Applied Spectroscopy*, vol. 47, No. 7 (1993) pp. 875-881.
Marbach, R. et al. "Optical Diffuse Reflectance Accessory for Measurements of Skin Tissue by Near-Infrared Spectroscopy," *Applied Optics*, vol. 34, No. 4, Feb. 1, 1995, pp. 610-621.
Mardia, K.V. et al., *Multivariate Analysis*, Academic Press (1979) pp. 300-325.
Martens, Harald et al., Updating Multivariate Calibrations of Process NIR Instruments, *Adv. Instru. Control* (1990) pp. 371-381.
McIntosh, Bruce C. et al. Quantitative Reflectance Spectroscopy in the Mid-IR, *16th Annual FACSS Conference*, Oct. 1989.
Nichols, et al., *Design and Testing of a White-Light, Steady-State Diffuse Reflectance Spectrometer for Determination of Optical Properties of Highly Scattering Systems*, Applied Optics, Jan. 1, 1997, 36(1), pp. 93-104.
Offner, A., "New Concepts in Projection Mask Aligners," *Optical Engineering*, vol. 14, No. 2, Mar.-Apr. 1975, pp. 130-132.

Osborne, B.G. et al., "Optical Matching of Near Infrared Reflectance Monochromator Instruments for the Analysis of Ground and Whole Wheat," *J. Near Infrared Spectrosc.*, vol. 7 (1999) p. 167.

Ozdemir, d. et al., "Hybrid Calibration Models: An Alternative to Calibration Transfer," *Appl. Spectros*, vol. 52, No. 4 (1998) p. 599.

Powell, J.R. et al, "An Algorithm for the Reproducible Spectral Subtraction of Water from the FT-IR Spectra of Proteins in Dilute Solutions and Adsorbed Monolayers," *Applied Spectroscopy*, vol. 40, No. 3 (1986) pp. 339-344.

Rafert, J.B. et al., "Monolithic Fourier-Transform Imaging Spectrometer," *Applied Optics*, vol. 34, No. 31, Nov. 1995, pp. 7228-7230.

Ripley, B.D. *Pattern Recognition and Neural Networks*, Cambridge University Press (1996) pp. 91-120.

Robinson, M. Ries et al., "Noninvasive Glucose Monitoring in Diabetic Patients: A Preliminary Evaluation," *Clinical Chemistry*, vol. 38, No. 9 (1992) pp. 1618-1622.

Royston, David D. et al., "Optical Properties of Scattering and Absorbing Materials Used in the Development of Optical Phantoms at 1064 NM," *Journal of Biomedical Optics*, vol. 1, No. 1, Jan. 1996, pp. 110-116.

Rutan, Sarah C. et al., "Correction for Drift in Multivariate Systems Using the Kalman Filter," *Chemometrics and Intelligent Laboratory Systems 35*, (1996) pp. 199-211.

Salit, M.L. et al., "Heuristic and Statistical Algorithms for Automated Emission Spectral Background Intensity Estimation," *Applied Spectroscopy*, vol. 48, No. 8 (1994) pp. 915-925.

Saptari, Vidi Alfandi, "Analysis, Design and Use of a Fourier-Transform Spectrometer for Near Infrared Glucose Absorption Measurement," (Massachusetts Institute of Technology, 1999) pp. 1-76.

Schmitt, J.M. et al., "Spectral Distortions in Near-Infrared Spectroscopy of Turbid Materials," *Applied Spectroscopy*, No. 50 (1996) p. 1066.

Service, F. John et al., Dermal Interstitial Glucose as an Indicator of Ambient Glycemia, *Diabetes Care*, vol. 20, No. 9, Sep. 1997, 9 pages.

Shroder, Robert, (Internet Article) MicroPac Forum Presentation, Current performance results, May 11, 2000.

Sjoblom, J. et al., "An Evaluation of Orthogonal Signal correction Applied to Calibration Transfer of Near Infrared Spectra," *Chemom & Intell Lab. Sys.*, vol. 44 (1998) p. 229.

Steel, W.H., "Interferometers for Fourier Spectroscopy," Aspen International Conference on Fourier Spectroscopy, (1970) pp. 43-53.

Sternberg R.S. et al., "A New Type of Michelson Interference Spectrometer," *Sci. Instrum.*, vol. 41 (1964) pp. 225-226.

Stork, Chris L. et al., "Weighting Schemes for Updating Regression Models—a Theoretical Approach," *Chemometrics and Intelligent Laboratory Systems 48*, (1999) pp. 151-166.

Sum, Stephen T. et al., "Standardization of Fiber-Optic Probes for Near-Infrared Multivariate Calibrations," *Applied Spectroscopy*, vol. 52, No. 6 (1998) pp. 869-877.

Swierenga, H. et al., "Comparison of Two Different Approaches Toward Model Transferability in NIR Spectroscopy," *Applied Spectroscopy*, vol. 52, No. 1 (1998) pp. 7-16.

Swierenga, H. et al., "Improvement of PLS Model Transferability by Robust Wavelength Selection," *Chemometrics and Intelligent Laboratory Systems*, vol. 41 (1998) pp. 237-248.

Swierenga, H. et al., "Strategy for Constructing Robust Multivariate Calibration Models," *Chemometrics and Intelligent Laboratory Systems*, vol. 49, (1999) pp. 1-17.

Teijido, J.M. et al., "Design of a Non-conventional Illumination System Using a Scattering Light Pipe," *SPIE*, Vo. 2774 (1996) pp. 747-756.

Teijido, J.M. et al., "Illumination Light Pipe Using Micro-Optics as Diffuser," *SPIE*, vol. 2951 (1996) pp. 146-155.

Thomas, Edward V. et al., "Development of Robust Multivariate Calibration Models," *Technometrics*, vol. 42, No. 2, May 2000, pp. 168-177.

Tipler, Paul A., *Physics, Second Edition*, Worth Publishers, Inc., Chapter 34, Section 34-2, Nov. 1983, pp. 901-908.

Wang, Y-D. et al., "Calibration Transfer and Measurement Stability of Near-Infrared Spectrometers," *Appl. Spectros.*, vol. 46, No. 5 (1992) pp. 764-771.

Wang, Y-D. et al., "Improvement of Multivariate Calibration Through Instrument Standardization," *Anal. Chem.*, vol. 64 (1992) pp. 562-564.

Wang, Z., "Additive Background Correction in Multivariate Instrument Standardization," *Anal. Chem.*, vol. 67 (1995) pp. 2379-2385.

Ward, Kenneth J. et al., "Syst-Prandial Blood Glucose Determination by Quantitative Mid-Infrared Spectroscopy," *Applied Spectroscopy*, vol. 46, No. 6 (1992) pp. 959-965.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471-476.

Whitehead, L.A. et al., "High-efficiency Prism Light Guides with Confocal Parabolic Cross Sections," *Applied Optics*, vol. 37, No. 22 (1998) pp. 5227-5233.

\* cited by examiner

ENCODED VARIABLE FILTER SPECTROMETER

RELATED APPLICATIONS

This application is related to U.S. patent application Ser. No. 09/832,585, entitled "System for Non-Invasive Measurement of Glucose in Humans"; U.S. patent application Ser. No. 09/832,586, entitled "Illumination Device and Method for Spectroscopic Analysis"; and U.S. patent application Ser. No. 09/832,608, entitled "Optically Similar Reference Samples and Related Methods for Multivariate Calibration Models Used in Optical Spectroscopy", all filed on the same date herewith and assigned to the assignee of the present application. The disclosure of each of these related applications is hereby incorporated by reference.

FIELD OF THE INVENTION

The present invention generally relates to optical spectrometers. More specifically, the present invention relates to encoded filter-based optical spectrometers.

BACKGROUND OF THE INVENTION

Optical spectrometers are systems that permit the measurement of optical intensity at specific wavelengths within a spectral region. In broad terms, a spectrometer can either measure each of the wavelengths individually, or it can measure multiple portions of the spectrum at one time. In the first case, the spectrometer operates in a sequential mode and is referred to as a scanning spectrometer system. In the latter case, the spectrometer is said to operate in a multiplexed fashion. Multiplexed spectrometers can be further divided into those that are based upon a detector array and those that use just a single detector. Array-based spectrometers incorporate some optical element such as a grating or prism to separate the light and distribute it across the detector array to record the individual intensities incident on the detector pixels. In contrast, a single-element multiplexing spectrometer incorporates an optical encoding subsystem such as an interferometer to encode the light in a manner that the resulting signal can be processed after collection to regenerate the individual spectral intensities. The subject of this disclosure is a new method for constructing a multiplexing spectrometer that is based on a single element detector, an optical filter assembly, and an encoding mask.

Spectroscopic measurement systems operating in the visible or near-infrared spectral regions may be used to measure a wide variety of sample characteristics that convey information regarding the presence and/or quantity of analytes. In particular, they can be used to measure analytes in inanimate samples, biological samples, and in human subjects. They can provide identifying information about the person or other sample type, provide information about the age, gender, or other demographic factors about the person being measured, provide information about the disease state of the person or sample being measured, or provide information about the quality or similarity of the sample being measured relative to some known population. In order to design and build a commercially viable spectroscopic system for these types of measurements, the spectrometer should be multiplexed and have high optical throughput in order to allow the spectroscopic system to collect as much light as possible in a given measurement time, and thereby increase the total measurement signal-to-noise ratio. The spectrometer system should also be stable to reduce the effect of instrument drift and reduce noise. Also, in order to facilitate the ability to perform a calibration on one instrument and use the same calibration model for other similar instruments (i.e. calibration transfer), the spectrometer system should be of a simple and robust design with a minimum number of components that have critical dimensions or require precise movement.

In addition, in order to facilitate efficient manufacture of such a spectrometer, it should contain few parts with a minimal number of adjustable critical dimensions. Ideally, the parts of the spectrometer would be well suited for large-scale manufacturing processes in order to fulfill the demands of large-volume production. It is also desirable that the parts of the spectrometer are manufactured using well-developed and well-understood technologies and materials to avoid unexpected interactions and effects when the parts are assembled into a complete spectrometer.

For broad commercial viability, the spectrometer should be designed to be as small and as inexpensive as possible. Due to the high cost of near-infrared detector arrays, a near-infrared spectrometer suitable for low-cost applications preferably will be based upon a single-element detector. In addition, the spectroscopic system must be rugged to withstand shock, dust, humidity and other adverse environmental influences.

There is a variety of spectrometers capable of being incorporated in a spectroscopic system to produce optical spectra which potentially can be used for analysis of analytes in biological media. Examples of suitable spectrometers include: diffraction spectrometers utilizing scanned or array diffraction gratings; refraction spectrometers utilizing a prism or mock interferometer; interference spectrometers utilizing a scanning Fourier Transform interferometer or stationary interferometer (e.g., Sagnac interferometer as described by Rafert, et al., *Monolithic Fourier-Transform Imaging Spectrometer*, Applied Optics, 34(31), pp 7228–30, 1995.); discrete light source spectrometers utilizing light emitting diodes, laser diodes or tunable diode lasers; and filter-based spectrometers utilizing acousto-optical transmission filters, liquid crystal filters, discrete optical filters, linear variable filters, or circular variable filters.

While each of these spectrometers is viable for generating spectra, each has shortcomings in terms of either optical throughput, stability, versatility, availability, size, or cost, depending upon the application. For example, in the case of using near-infrared spectra (1.25–2.5 µm) to measure analytes in biological media, Fourier Transform instruments that provide high optical throughput, high stability, high versatility and are readily available tend to be large and relatively expensive. While design improvements can be made to reduce size and cost while maintaining the other desirable characteristics of an FTIR system for this application, other methods for generating spectra with fewer, less costly parts could be competitive with the FTIR approach.

One such alternative is the use of optical filters. There are commercially available assemblies for spectral separation and detection that use optical filters, such as the MicroPac assembly available from Optical Coating Laboratories, Inc. (OCLI), as schematically shown in FIG. 1. The MicroPac assembly 10 receives light or radiation 12 through a dielectric linear variable filter (LVF) 14, micro-optics 16 and a detector array 18. The LVF 14 is a bandpass dielectric filter whose properties vary over its length such that the central wavelength of the pass band varies linearly across the filter 14. OCLI's MicroPac assembly 10 images the LVF 14 onto the detector array 18 to generate a spectrum of the light incident on the LVF 14. The cost of the MicroPac assembly 10 that can be used for visible and/or very near infrared regions is significantly affected by the price of the particular silicon detector array utilized. Due to the relative scarcity and high cost of NIR arrays that can detect light with a wavelength as long as 2.5 μm (e.g., InGaAs or PbS), the NIR embodiment of the OCLI MicroPac assembly is expensive.

During the proceedings of the MicroPac Conference hosted by OCLI in California, on May 11$^{th}$ and 12$^{th}$, 2000, Shroder proposed the use of a fiber optic coupling to increase efficiencies of the assembly 10 by twenty (20) to forty (40) times. See *Current Performance Results* by Robert Shroder, MicroPac Forum Presentation, May 11, 2000. However, in all instances, the OCLI assembly 10 is used on the detector side of a spectrometer just prior to the detector array. It has not been suggested to use the LVF 14 on the illumination side of the system, prior to the sample under analysis, nor has it been suggested to include the LVF with an integrating chamber for coupling a light source to an encoded filter-based spectrometer.

Another approach used in spectrographic analysis is to incorporate a Hadamard or other encoding mechanism in a spectrometer to enable multiplexing and thereby increase the overall optical throughput of the system, as is known in the art. For example, Harwitt and Sloan (Harwit, M. and N. Sloan, Hadamard Transform Optics, pages 109–145, Academic Press, 1979) discuss the application of a Hadamard mask to either or both the entrance and exit planes of a grating spectrometer. However, such prior art does not indicate that the encoding can be combined favorably with a filter-based instrument.

U.S. Pat. No. 6,031,609, entitled "Fourier Transform Spectrometer using a Multielement Liquid Crystal Display," teaches a system and method for combining prisms or gratings with a liquid crystal spatial light modulator in such a way as to create a Fourier Transform spectrometer. The advantages claimed for this system include increased signal-to-noise ratios over scanning dispersive instruments for a fixed integration time without any moving parts. However, such prior art does not indicate that multiple encoding methods and systems can be applied for encoding, or that the encoding can be combined favorably with a filter-based instrument.

From the foregoing, it should be apparent that there is an unmet need for an encoded filter-based spectrometer that optimizes optical throughput, stability, versatility, availability, size, and cost.

SUMMARY OF THE INVENTION

The present invention provides a spectrometer capable of being incorporated into a small, simple, rugged, inexpensive spectroscopic system for commercial applications. The spectrometer of the present invention optimizes optical throughput, increases the signal-to-noise ratio of the system, and decreases the complexity of the system. The spectrometer of the present invention is well suited for incorporation in a spectroscopic system that collects data necessary to perform spectroscopic determinations on biological media. Spectroscopic determinations include measuring the quantity of an analyte, the presence or absence of an analyte, checking for sample quality and consistency with a known class of samples, performing classification of disease states, estimation of age and gender, and establishing identity via individual spectroscopic markers. Biological media includes living tissue, excised tissue, and fluids measured either in-vivo or in-vitro derived from humans, animals and other living organisms. Any of these spectroscopic measurements can be made using either diffuse reflectance or transmission measurement optical sampling geometries.

The present invention provides a number of different spectrometers for use in spectroscopic systems. The spectroscopic systems of the present invention basically include a light source for generating light and a detector for receiving light. The light source can include a multiwavelength tungsten-halogen emitter, an array of LED infrared emitters, a flashlamp, an arc lamp or any other illumination source. Each spectrometer configuration also preferably includes a means to encode the light emitted by the source. As well, each spectrometer also preferably includes a single or multiple variable optical bandpass filter(s) with properties that vary with position, such as a linear variable filter (LVF), or an optical filter assembly that includes a number of discrete filters with two or more different optical bandpass regions for receiving and filtering light from the source. Light that strikes the filter within the bandpass region is transmitted through the filter over a specific area or region, and the light outside the bandpass region is substantially reflected back.

In addition, each spectrometer may include an integrating chamber that collects and redirects light that is emitted from the source and does not pass through the filter. The integrating chamber essentially boosts the optical throughput of the spectroscopic system and increases the signal-to-noise ratio. The integrating chamber may allow direct illumination of the filter from the light source and also allows the light reflected back from the filter to make additional attempts to pass through the filter. The integrating chamber maximizes the return of the reflected light to the filter assembly and minimizes optical losses. By increasing the optical throughput and minimizing optical losses, the spectrometer may be arranged in the spectroscopic system such that the sample is disposed adjacent to either the detector or the light source.

The light source may be positioned inside or outside the integrating chamber. If the light source is located outside the integrating chamber, the integrating chamber may be of an orthogonal design (i.e., cuboid or cylindrical) to preserve the optical geometric characteristics of the light entering the integrator, even after multiple reflections from the filter. This is beneficial if it is necessary to maintain the angular distribution of the light entering into any of the subsequent optical components of the spectrometer system. Alternatively, a round, polygonal, conical or irregular shape may be used if it is desired to homogenize the light from the source. Further, the integrator may have at least a portion that is shaped to focus light over a desired specific area.

The bandpass filter may be selected and adjusted to optimize light throughput in the system. Aspects of the system that can be optimized by the choice of the variable filter or filter assembly include maximizing the amount of light in spectral regions important to the measurement being made, reducing photon noise by eliminating light in spectral regions outside the band(s) of interest, and optimizing the spectral properties of the light passing through the tissue or other sample type to reduce or eliminate optically induced damage to the sample. The filter may comprise a variable filter or a selection of discrete bandpass filters. In addition, the filter may comprise a linear or non-linear variable filter.

The output of a linear variable filter is generally distributed spatially over a relatively large area. In one embodiment, a first integrating chamber is used to receive light from the source and passes this light to a first linear variable filter. Light passing through the appropriate bandpass of the linear variable filter then passes to an encoding unit. Light exiting the encoding unit strikes a second linear variable filter having a spatial distribution of wavelength passbands matching those of the first linear variable filter. Light passing through the appropriate portion of the second linear variable filter enters a second integrating chamber which allows light from the large linear variable filter surface area to be efficiently collected into a smaller exit port. This allows for a dramatic reduction in the size of the fiber optic bundle and/or detector which would otherwise receive the light exiting the relatively large surface area of the linear variable filter.

The encoding unit is a spatial light modulator that may comprise a movable (linear or rotating) mask having an aperture array, a liquid crystal spatial light modulator, a micro-electromechanical system (MEMS), a digital mirror device (DMD) or any other equivalent method for spatial modulation of the light. In addition, the filter and the encoding unit may be combined into a single unit.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
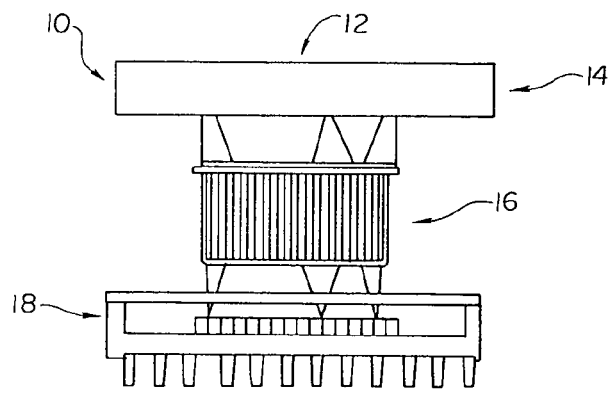
FIG. 1 is a schematic illustration of the MicroPac assembly.
Figure 2:
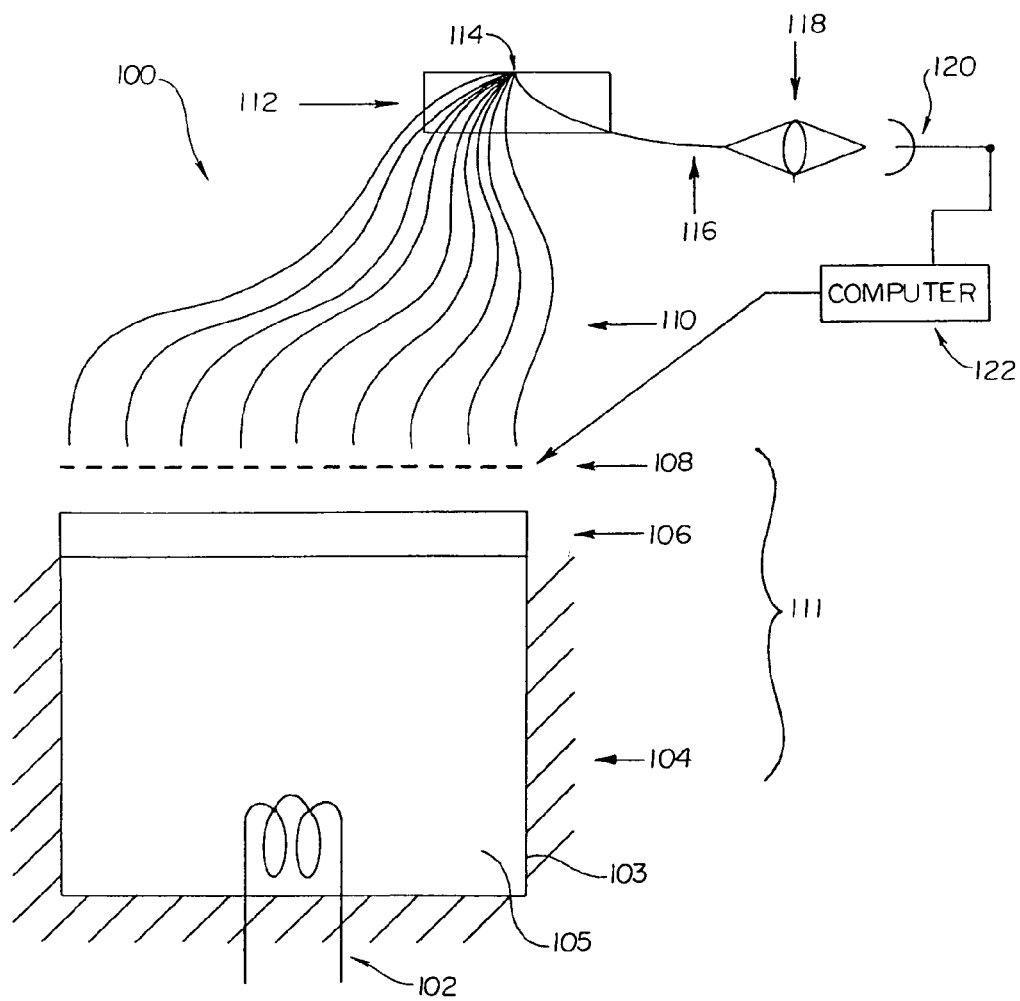
FIG. 2 is a schematic illustration of a spectrometer system utilizing a basic encoded variable filter device in accordance with an embodiment of the present invention.

Refer now to FIG. 2, which is a schematic illustration of a spectrometer system 100 utilizing a basic encoded variable filter (EVF) device 111 in accordance with an embodiment of the present invention. Note that spectrometer components 106/108 are collectively referred to as encoded variable filter (EVF) device or unit 111. Further, component 104, the integrating chamber, is an optional component included in encoded variable filter device 111. The spectrometer 100, in a preferred embodiment, includes an optical light source 102, an optical integrating chamber 104, a filter assembly 106 such as a linear variable optical bandpass filter, a spatial encoding device 108, a sampler 112 incorporating illumination optical fibers 110 that shine light into the tissue at the sampler/tissue interface 114 and detection optical fibers 116 that detect light after passing through the tissue (in either reflectance or transmission), a lens 118, a detector 120, and a computer 122 to control the spatial encoding unit 108 and to collect the detected optical signal from the detector 120. The computer 122 includes the basic components of a processor, a memory for storing data and software, an input device and an output device.

As shown, the spectrometer system 100 is arranged with the sampler 112 and sample interface 114 between the spectrometer components 102–110 and the detector 120 (source-spectrometer-sample-detector). Those skilled in the art will recognize that all embodiments described herein may be arranged with the sampler 112 and sample interface 114 between the light source 102 and the spectrometer components 104–120 (source-sample-spectrometer-detector). The illustrated configuration (source-spectrometer-sample-detector) of the system 100 is especially suitable for diffuse reflectance tissue sampling due to the highly attenuating nature of the tissue. In the near infrared, one watt of light incident on the tissue will yield between 1 and 100 micro-watts of light that is available for detection (the exact ratio depends upon the wavelength, the exact sampler geometry, and other factors). Due to the large optical losses caused by attenuation and scatter by tissue, it is advantageous to minimize instrumental losses between the exiting light at the tissue interface 114 and the detector 120. Thus, placing the spectrometer components 102–110 prior to the sampler 112 and sample interface 114 removes a potentially large loss in the detection channel. The illustrated configuration of the system 100 is optimal if the illumination source 102 and spectrometer components 106/108 can produce enough optical power such that the sample (e.g., skin tissue) can be illuminated at a level below the sample damage threshold.

In a preferred embodiment, the optical filter assembly 106 is constructed from one or more dielectric filters in such a way that light that is not passed through the filter is substantially reflected. In this preferred embodiment, the optical integrator or integrating chamber 104 is incorporated in the EVF unit 111 to take advantage of the dielectric optical filter

106 which, over its surface area, includes regions which transmit light with a single, well-defined band of optical wavelengths. With the dielectric filter 106, light outside the bandpass region in a specific portion of the surface area is substantially reflected and would represent a significant optical loss but for the integrating chamber 104. In the present invention, the integrating chamber 104 is used to capture and redirect the light that is outside the bandpass region of a portion of the filter 106 to other portions of the filter appropriate for the wavelength region, resulting in a significant increase in the optical power passing through the filter 106.

The integrating chamber 104 comprises a hollow shell 103 defining an interior 105. The inside surface of the shell 103 comprises a reflective material or coating such that light entering the interior 105 is reflected off of the inside surface of the shell 103 until the light exits the integrating chamber 104. Alternatively, the integrating chamber 104 can be a light-transmitting solid, such as glass or a liquid-filled chamber, each with a reflective surface 103. The reflective surface(s) of the integrating chamber may be optically smooth, providing specular reflections, or optically rough, providing diffuse reflections. To preserve angular characteristics of the light, the reflective surfaces of the integrating chamber 104 may be made optically smooth and the shell may be of orthogonal design. Orthogonal design means that the walls of the integrating chamber 104 are orthogonal to the filter 106 and encoding unit 108 (i.e., cuboid or cylindrical integrating chamber), although other shapes (e.g., spherical, oblong, etc.) are also feasible. The light source can also be placed within the integrating chamber 104.

Further, an integral unit could be used wherein the glass envelope holding the bulb filament is designed as an integrating chamber having the above features.

In a preferred embodiment, the optical integrator 104 may boost the optical throughput of the spectrometer system 100. The optical integrator 104 may allow light from the light source 102 to directly illuminate or strike the variable filter assembly 106 and also allows the light rejected (i.e. reflected) from the variable filter assembly 106 or the spatial encoding unit 108 to make additional attempts to pass through the filter 106. The optical integrator 104 is designed to maximize the return of the reflected light to the filter assembly 106 with a minimum of optical losses. In addition, in cases where the light source 102 is located outside of the integrating chamber 104, the integrating chamber 104 may be fabricated as a reflective cuboid, which will preserve the optical geometric characteristics of the light entering the integrator 104 even after multiple reflections from the filter 106 surface.

The optical light source 102, such as a quartz tungsten halogen lamp, may be located inside the optical integrating chamber 104. Alternatively, the light source 102 may be located outside the optical integrating chamber 104, with all or a portion of the emitted optical radiation from the light source 102 directed into the integrating chamber 104 using lenses, mirrors or other optical means with substantially the same effect.

The dielectric bandpass filter assembly 106 may be made of a single linear variable filter, two or more linear variable filters, a circular variable filter (or segment thereof), a variable filter embodying a nonlinear bandpass profile, or a plurality of individual optical bandpass filters fabricated as separate pieces. The optical filter(s) 106 may be dielectric and be positioned such that light that is not of the proper wavelength for transmission by a filter element (or a portion of the filter) is substantially reflected back into the integrating chamber 104. In so doing, the reflected light can be redirected to impinge on a different filter element (or portion of the filter), thereby substantially increasing the optical throughput of the system 100. Other filters could also be utilized, including absorbance filters, metallic filters or tunable filters.

Figure 3:
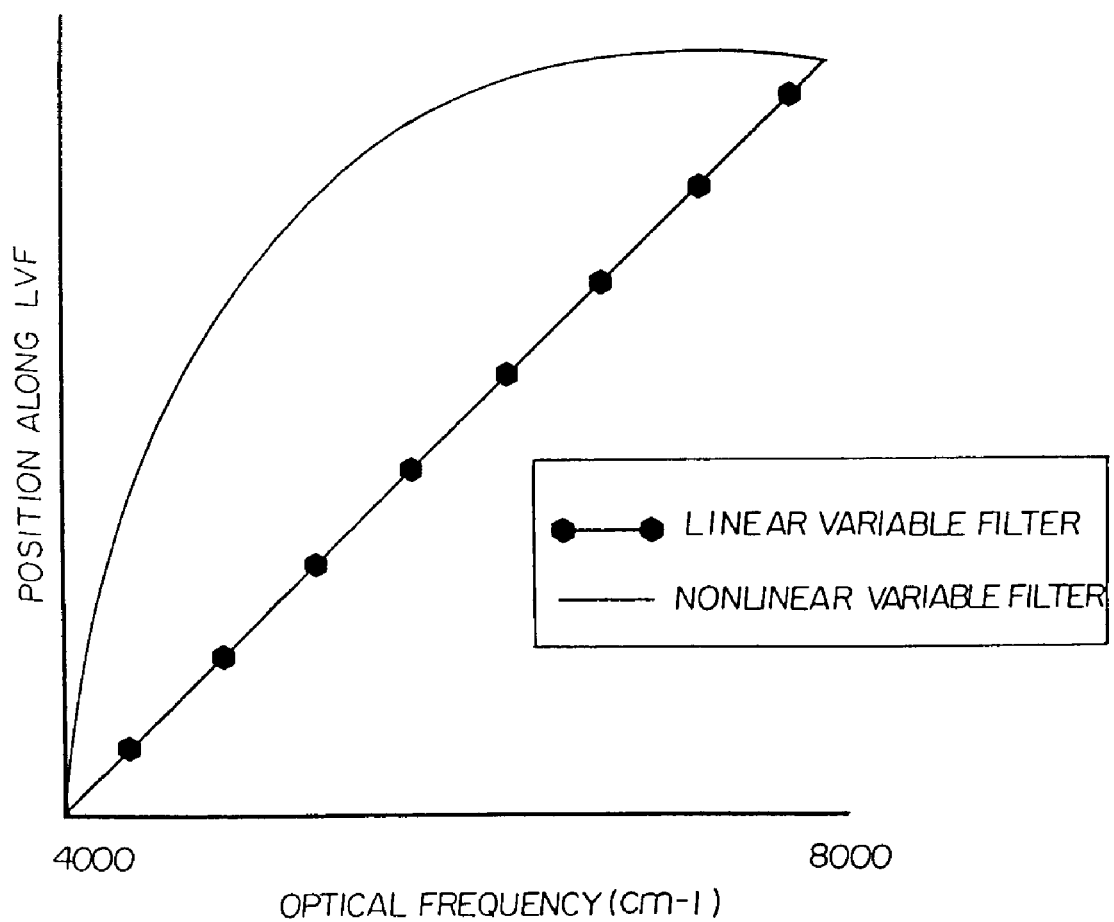
FIG. 3 is a graph comparing linear and non-linear variable filters.

A variable optical filter 106 having a nonlinear bandpass profile may be utilized to pass more light of desirable wavelengths and less light of less desirable wavelengths. FIG. 3 is a graph showing a representative distribution of multiple wavelength light passing through a linear and non-linear variable filter. The vertical axis is the position along the variable filter and graphically illustrates a design wherein a greater portion or area of the filter is devoted to passing light in spectral regions of more importance to the analysis. As an alternative, a plurality of discrete filter elements may be used to pass more light of desirable wavelengths and less light of less desirable wavelengths by selecting the appropriate number and type of bandpass filter elements (central wavelengths and optical widths). These filter elements can be arranged in a non-ordered or ordered arrangement as appropriate to other characteristics of the design or manufacture of the EVF unit. The dielectric filter(s) 106 may be positioned such that each distinct filter element is proximal to, or can be imaged onto, a different location of the spatial encoding unit 108.

One means of determining the configuration of a non-linear variable optical filter is to interrogate the final regression coefficients (FRC) of a spectroscopic system. Those wavelengths at which the FRC has a large absolute magnitude are the wavelengths that are most heavily weighted by the system to produce the analyte estimate. For this reason, the signal-to-noise at each of these strongly-weighted wavelength bands will have the greatest influence on the resulting prediction error. A non-linear filter can be used to adjust the distribution of light such that strongly FRC-weighted wavelength bands are given a larger spatial segment of the filter. In general, the incorporation of a new non-linear filter in a spectroscopic system will alter the resulting FRC. Therefore, if desired, this new system and its corresponding FRC can then be the basis for a new non-linear filter optimization. This iterative calculation of the non-linear filter design can then be repeated as necessary to achieve the desired level of refinement. The use of an end-to-end computer model of the system can be used to facilitate this iterative design process, rather than relying on multiple hardware/experimental iterations.

The spatial encoding unit 108 comprises a spatial filter that encodes each physical location on the optical bandpass filter(s) 106, which in turn corresponds to a different optical frequency. The encoding unit 108 may utilize a Hadamard transform, a Fourier amplitude modulation, a Fourier frequency modulation, a random coding pattern, or any other similar variant. Devices suitable for this type of encoding unit 108 include electromechanical aperture arrays (circular motion or linear), liquid crystal spatial light modulators, micro-electromechanical systems (MEMS), digital mirror devices (DMDs) also known as Digital Light Processors (DLPs), and others described in more detail hereinafter.

In a preferred embodiment where the encoded variable filter device 111 includes an integrating chamber 104, the source side of the spatial encoding unit 108 may be made optically reflective and oriented in such a way that light that is blocked by the encoding unit 108 is substantially reflected toward the integrating chamber 104. In this way, light that passes through the variable filter 106 but blocked by the encoding unit 108 will enter the integrating chamber 104 and be redirected. This light will then have a chance to pass through another suitable portion of the filter 106 that could correspond to an open portion of the encoding unit 108.

The order of the EVF device 111 components in FIG. 2 and subsequent figures is depicted as a light source 102, followed by a variable filter assembly 106, followed by a spatial encoding device 108. Those skilled in the art will recognize that all embodiments described herein may also be arranged with the light source 102, followed by the spatial encoding device 108, followed by the variable filter assembly 106.

The optical filter 106 and the encoding unit 108 may be combined into a single unit, which offers the possibility of additional encoding schemes. For example, if the encoding unit 108 comprises a MEMS device or other electromechanical system which encodes the light in such a way that the light passing through a particular encoding aperture is passing through either one of two different optical bandpass filters, then the encoding unit may have half the number of encoding apertures and encoding mechanisms, and therefore require half the space. Specific embodiments of a combined filter 106 and encoding unit 108 are described in more detail hereinafter.

The spectroscopic measurement system 100 is particularly suitable for operating in the visible or near-infrared spectral regions to measure or identify a wide variety of analytes such as glucose, urea, ethanol, beta2 microglobulin, different hemoglobin types, hematocrit, other biological analytes and specific or overall tissue properties (for biometric identity applications). Other applications can include age verification, gender verification, disease state determinations, tissue hydration estimation, and sample similarity assurance. For purposes of illustration only, use of the spectrometer system 100 is described in terms of measuring glucose concentration through skin tissue. An example of this application is described in U.S. Pat. No. 4,975,581 to Robinson et al., the disclosure of which is hereby incorporated herein by reference. Other exemplary applications include those disclosed in U.S. Pat. No. 5,494,032 to Robinson et al; U.S. Pat. No. 5,596,992 to Haaland et al., the disclosures of which are incorporated herein by reference. Further applications are disclosed in commonly assigned pending applications including U.S. patent application Ser. No. 09/832,585, filed on the same day herewith, entitled "System for Noninvasive Measurement of Glucose in Humans"; U.S. patent application Ser. No. 09/182,340, filed Oct. 29, 1998, entitled "Apparatus and Method for the Determination of the Adequacy of Dialysis by Non-Invasive Near-Infrared Spectroscopy'" and U.S. patent application Ser. No. 09/4 15,594, filed Oct. 8, 1999, entitled "Apparatus and Method for Identification of Individuals by Near-Infrared Spectrum", the disclosures of which are each incorporated herein by reference.

In use, the sampler 112 is positioned adjacent the skin tissue to form a tissue interface 114. The light source 102 is then activated to pass light through the integrating chamber 104 and into the filter 106. Light having a wavelength within the acceptable bandwidth passes through the filter 106, and light of unacceptable wavelength is reflected back into the integrating chamber 104 where it is ultimately retransmitted to the filter 106. Light within the acceptable bandwidth passes through the filter 106 and into encoding unit 108 which may be controlled by the computer 122. The encoding unit 108 correlates discrete locations on the filter 106 to the encoding unit 108. This can also correlate filter locations to discreet or multiple optical fibers, such that each optical fiber 110 or group of optical fibers represents or receives a specific frequency of light. Alternatively, optical components such as lenses, mirrors, or light pipes can be incorporated in the system between the output of the EVF 111 and the optical fibers 110 to collect substantially all of the encoded light and redirect it into the sampler input fibers such that no specific frequency-fiber relationship exists.

The filtered light is then transmitted through the optical fibers 110 to the sampler 112, which includes input and output elements (not shown). Light is delivered into the skin tissue at the tissue interface 114 through the input element of the sampler 112. A portion of the light that is not absorbed by the tissue at the tissue interface 114 is collected by the output element of the sampler 112. The collected light is then transmitted through the detection optical fiber 116, through the lens 118, and to the detector device 120. The detector device 120 converts the light signal into an electric signal, which is representative of the non-absorbed light. The detector can be an InGaAs, silicon, InSb, PbSe, Ge, Si, a bolometer or any other suitable detector and can consist of one or more detector elements. The electric signal from the detector 120 is transmitted to and processed by the computer 122 which decodes the signal and provides a measure of the analyte (e.g., glucose concentration) of interest.

It is also possible to use the raw encoded data directly for some spectroscopic measurements. This capability decreases the processing power and cost of components necessary for a stand-alone spectral system 100 and improves the response time of the system 100.

Figure 4:
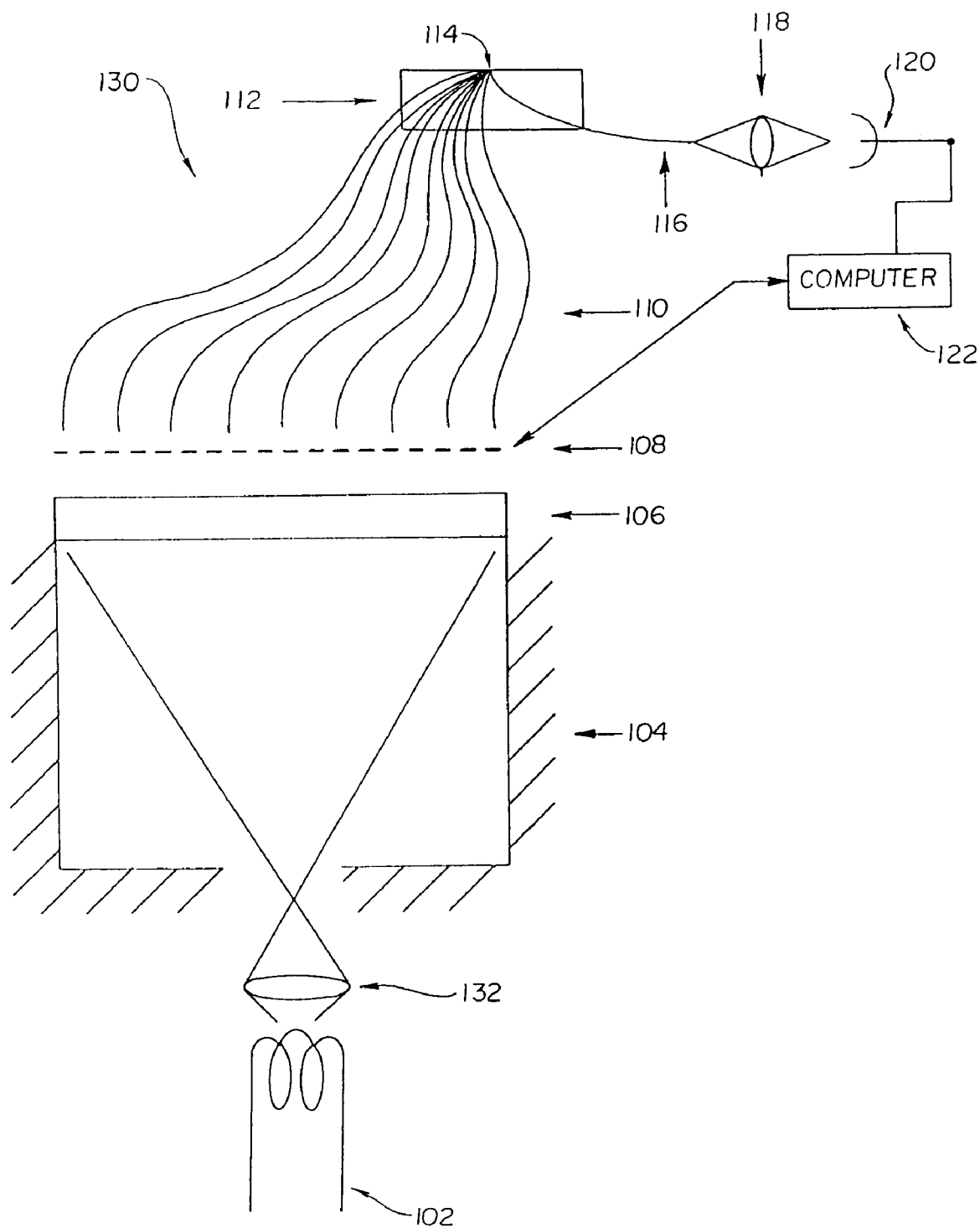
FIG. 4 is a schematic illustration of a spectrometer system utilizing an external source interfaced with imaging optics in accordance with an embodiment of the present invention.
Figure 5:
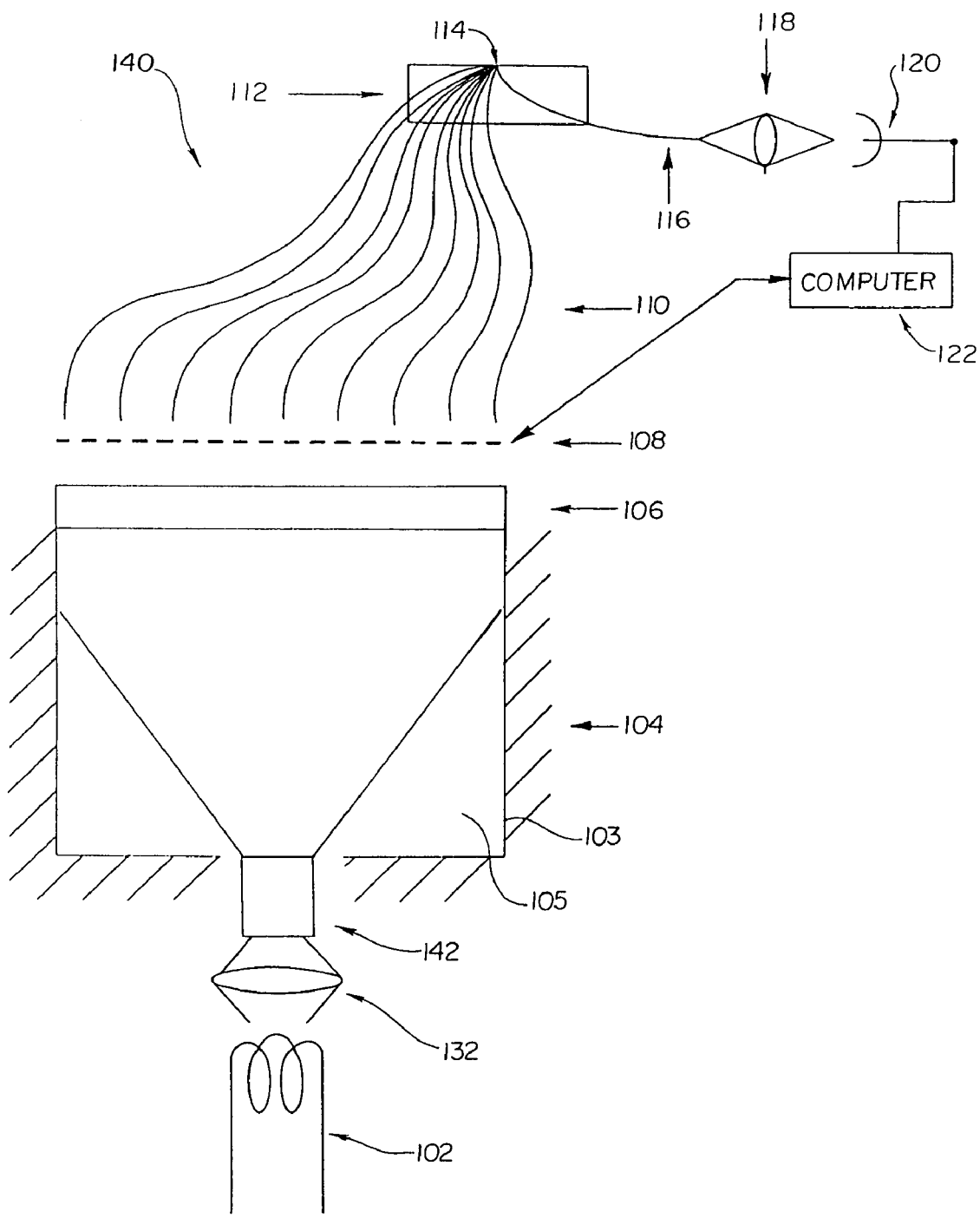
FIG. 5 is a schematic illustration of a spectrometer system utilizing an external source interfaced with non-imaging optics in accordance with an embodiment of the present invention.

Refer now to FIGS. 4 and 5, which are schematic illustrations of spectrometer systems 130/140 utilizing an external light source 102. Except as described herein, the design, function and use of the spectrometer systems 130/140 are substantially the same as described with reference to the spectrometer system 100 illustrated in FIG. 2. The external light source 102 may be located remotely and interfaced with the integrating chamber 104 using imaging optics 132 as shown in FIG. 4, and/or non-imaging optics 142 as illustrated in FIG. 5. The imaging optics 132 may comprise refractive or reflective optics to aid in collecting and directing the light emitted by the light source 102 into the integrating chamber 104. The non-imaging optics 142 may comprise a light pipe, a fiber bundle or other similar device to transmit the light emitted by the light source 102 into the integrating chamber 104. Some types of non-imaging optical devices 142, such as a light pipe, allow the light emitted by the light source 102 to be scrambled and homogenized. An example of a suitable light pipe is disclosed in commonly assigned U.S. patent application Ser. No. 09/832,586, filed on the same date herewith, entitled "Illumination Device and Method for Spectroscopic Analysis," the entire disclosure of which is incorporated herein by reference. Such a light pipe both spatially and angularly homogenizes light such that the system is insensitive to variation inherent in the light source which has been shown to negatively impact the predictive capability in spectroscopic analysis of tissue.

With either of the spectrometer systems 130/140 illustrated in FIGS. 4 and 5, respectively, the integrating chamber 104 may be of orthogonal design with smooth reflective interior sides to preserve the angularity of the light entering the integrating chamber 104. Previously disclosed shapes for the chamber can also be utilized. However, when the illumination optical fibers 116 and filter 106 are matched to apertures of the imaging/non-imaging optics 132/142, the orthogonal integrating chamber 104 is particularly beneficial because the preservation of angular characteristics maintains the desired match when light passes through the integrating chamber 104. In preferred embodiments, optical fibers which receive a preferred angular range of light are utilized to eliminate unwanted angles. Optical baffles can also be included in the output end of the integrating chamber to limit the angular distribution of the light leaving the chamber.

As mentioned previously, the filter 106 and encoding unit 108 may comprise a wide variety of designs, some of which are described with reference to FIGS. 6–13. Except as described herein, the design, function and use of the spectrometers systems 150/160/170/190/200/210/220 illustrated in FIGS. 6–13 are substantially the same as described with reference to the spectrometer system 100 illustrated in FIG. 2.

Figure 6:
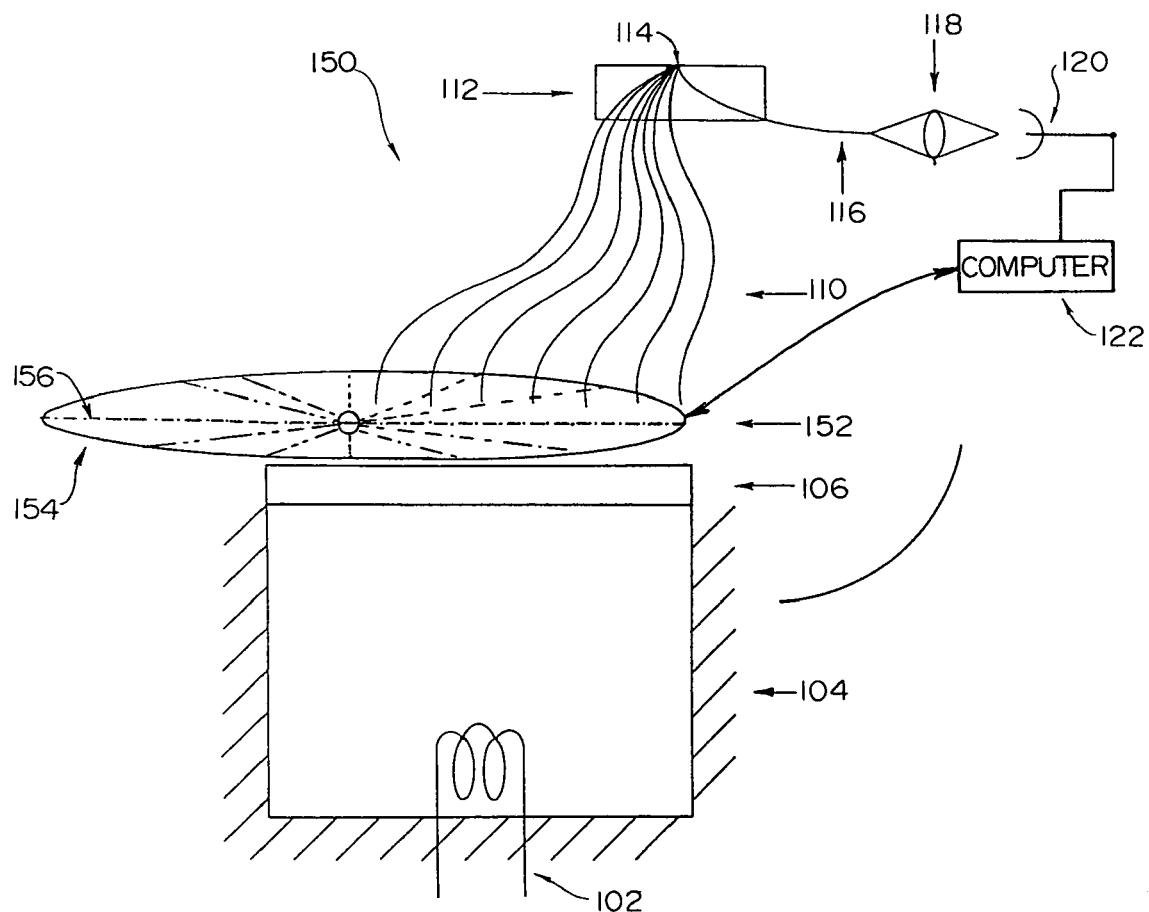
FIG. 6 is a schematic illustration of a spectrometer system utilizing a rotating mask encoding system in accordance with an embodiment of the present invention.

Refer now to FIG. 6, which is a schematic illustration of a spectrometer system 150 utilizing a rotating mask 152 encoding system. The rotary encoding mask 152 comprises a disc including a plurality of apertures 156 arranged in varying patterns in radial lines which align with selected portions of the LVF 106 at specific times when the mask 152 is rotated as shown. The position of the apertures 156 may be changed to perform the spectral encoding. Rotation of the rotary mask 152 is synchronized with the data collection system 122, and may be continuous or stepped. The bottom side 154 of the mask 152 is highly reflective to return blocked light into the integrating chamber 104 for an additional chance to pass through to the filter 106. The mask 152 may alternatively be linearly translated in order to perform the spatial encoding. Further, the mask 152 location and filter 106 order can be switched, but it would be desirable to make the mask highly reflective on both sides if placed between the source and filter.

Figure 7:
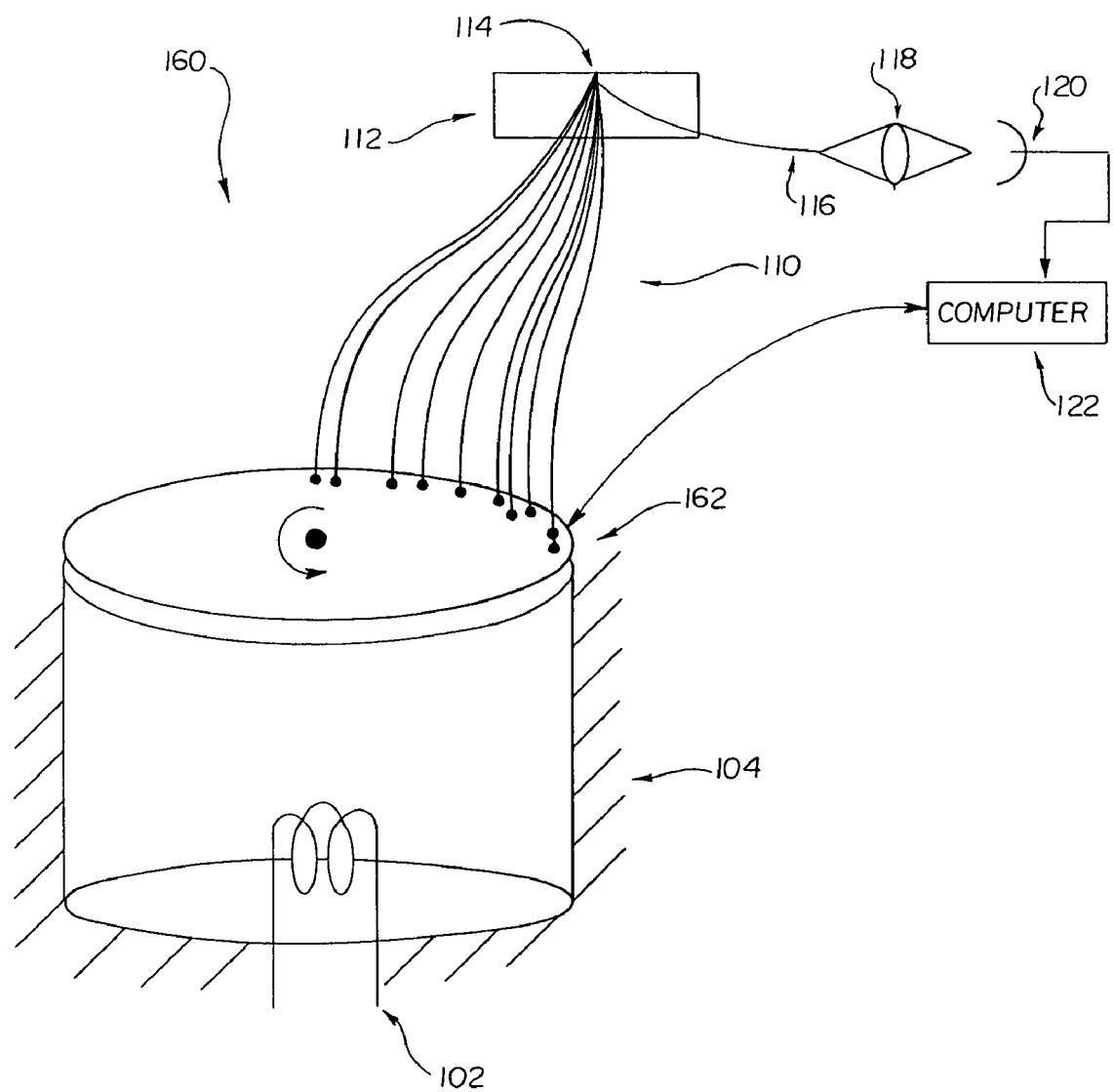
FIG. 7 is a schematic illustration of a spectrometer system utilizing a rotating circular variable filter (CVF) encoding system in accordance with an embodiment of the present invention.

Refer now to FIG. 7, which is a schematic illustration of a spectrometer system 160 utilizing a rotating circular variable filter (CVF) encoding system 162. The CVF encoding system 162 is similar to the rotating mask 152 encoding system described above, except that the CVF encoding system 162 rotates and the illumination fibers 110 act as the aperture/mask set. In a preferred embodiment, the space around each of the fibers is filled with a reflective material that redirects the light passing through the CVF 162 back into the integrating chamber 104 if it does not enter a fiber 110. The position of the illumination fibers 110 may be varied and the CVF 162 is rotated to perform the spectral encoding. For example, the spacing of the fibers 110 at the CVF 162 may be chosen to define a Hadamard cyclic mask. In this particular embodiment, the integrating chamber 104 may be cylindrically shaped as shown which will also preserve the angular characteristics of the light and could be used with the embodiments of FIG. 4 and FIG. 5.

Those skilled in the art will recognize that the inventive aspect of the encoding mechanism depicted in FIG. 7 can also be achieved by holding the CVF 162 stationary and moving the optical fibers 110 in an appropriate manner. This same method of encoding can also be applied to many of the other encoding methods described in the figures. For example, a filter assembly 106 can be combined with a set of optical fibers 110 with an additional mechanism (not shown) to move the fibers such that each fiber can be positioned to accept more or less of the light passing through a particular location of the filter assembly 106. In this way, an encoding can be implemented by varying the position of each fiber separately.

Figure 8:
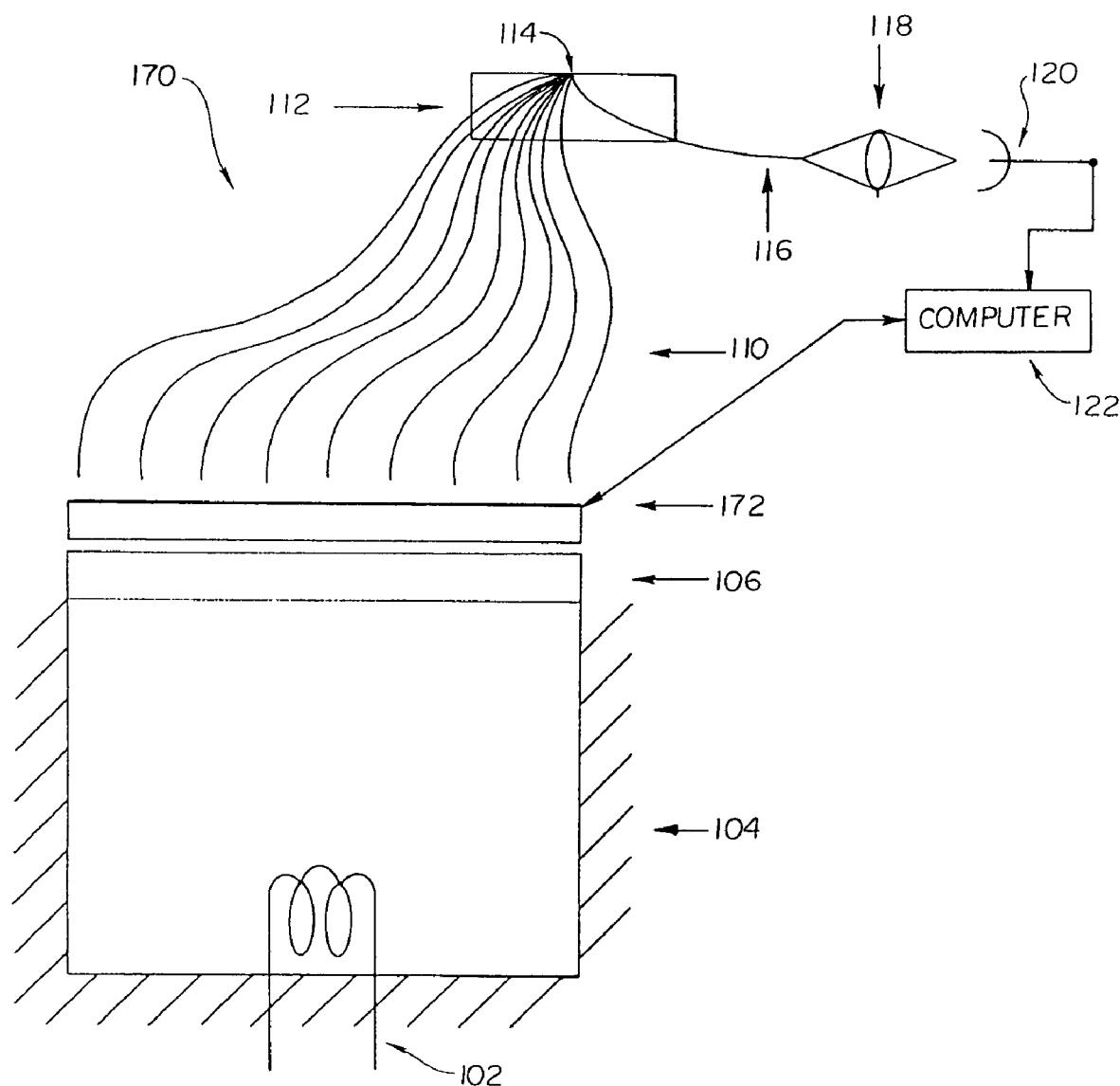
FIG. 8 is a schematic illustration of a spectrometer system utilizing a liquid crystal encoding system in accordance with an embodiment of the present invention.

Refer now to FIG. 8, which is a schematic illustration of a spectrometer system 170 utilizing a liquid crystal encoding system 172 in combination with the filter 106 to produce the spectral encoding. The liquid crystal encoding system 172 comprises a liquid crystal spatial light modulator having a plurality of liquid crystal elements (not shown). Each liquid crystal element of the liquid crystal encoding system 172 is individually addressed and controlled by the computer 122 to perform the encoding by individually modulating the amplitude of the light passing through each element.

Figure 9:
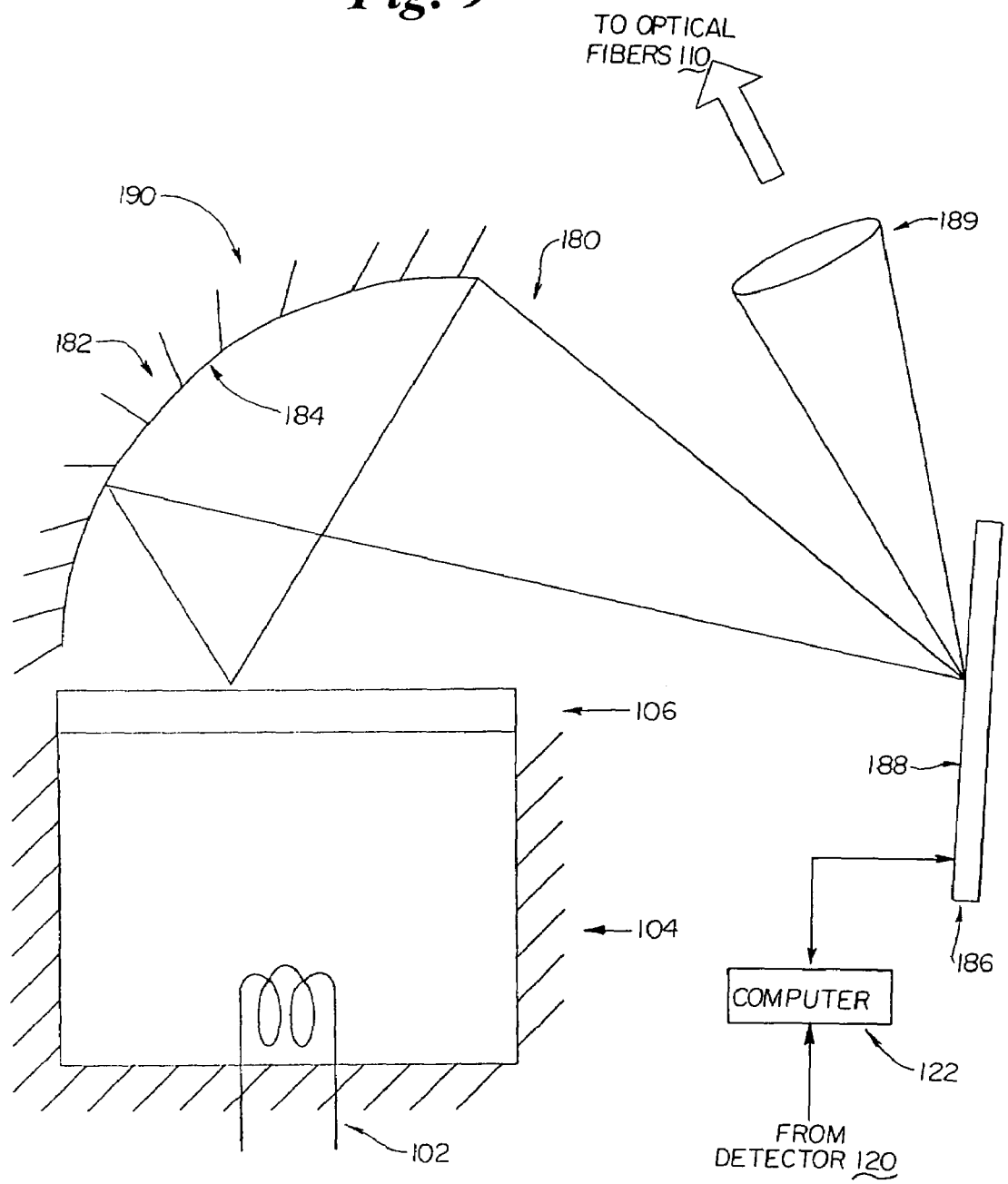
FIG. 9 is a schematic illustration of a spectrometer system utilizing a digital mirror device (DMD) encoding system in accordance with an embodiment of the present invention.

Refer now to FIG. 9, which is a schematic illustration of a spectrometer system 190 utilizing a digital mirror device (DMD, also known as a digital light processor or DLP) encoding system 180 in combination with the variable filter 106 to produce the spectral encoding. The DMD encoding system 180 utilizes a concave mirror 182 having a reflective surface 184 to direct light to a DMD 186. The DMD 186 comprises a plurality of individual mirrors (not shown) having reflective surfaces 188. The position of each individual mirror of the DMD 186 is controlled by the computer 122 to perform the encoding. Light reflected from the DMD 186 is either transmitted to the illumination fibers 110 through a focusing lens 189 or directed elsewhere, depending on the position of the particular DMD encoding mirror. Although not shown, the optical fibers 110, sample holder 112, detector 120, etc., are arranged the same as illustrated in FIG. 2. Those skilled in the art will recognize that the DMD device and optical system shown in FIG. 9 can be arranged such that light that is not transmitted to the optical fibers 110 by a particular element of the DMD 188 can be substantially reflected back through the variable filter assembly 106 and into the integrating chamber 104 resulting in additional chances for the light to pass through the system in adjacent portions of the variable filter assembly 106, thereby increasing optical efficiency. Alternatively, one or more additional samplers 112, lenses 118, and detectors 120 may be configured such that light that is reflected by a particular DMD element is being directed into one of the optical fiber bundles 110 at all times. In this way, complementary spectral data sets are generated by each of the detectors 120.

Figure 10:
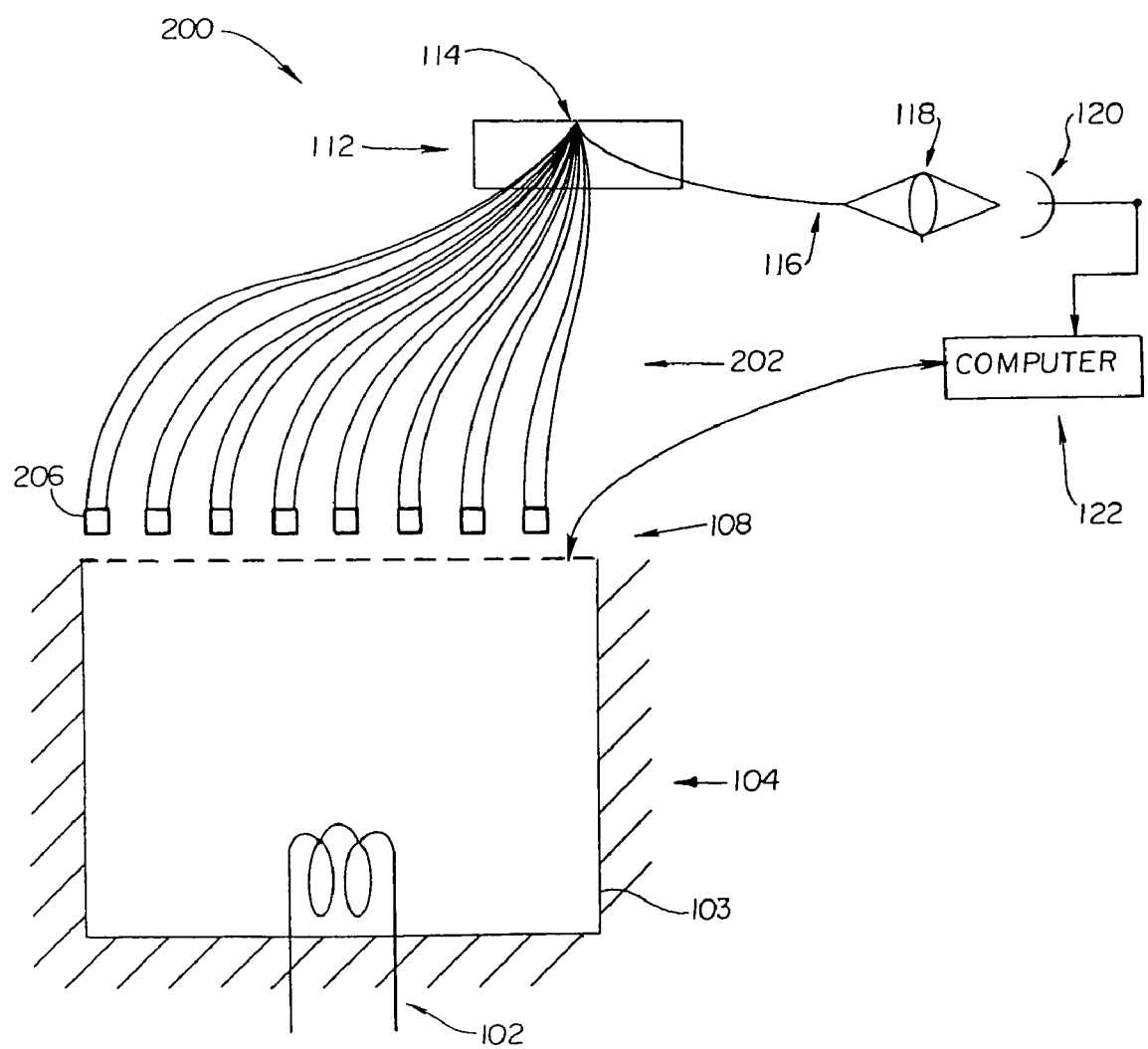
FIG. 10 is a schematic illustration of a spectrometer system utilizing optical fibers with integral bandpass filters in accordance with an embodiment of the present invention.

Refer now to FIG. 10, which is a schematic illustration of a spectrometer system 200 utilizing optical fibers 202 with integral bandpass filters 206. Different optical bandpass filters 206 may be applied directly to each illumination fiber 202 using either conventional coating techniques or using distributed Bragg phase gratings as described by Kashyap andRaman in *Fiber Bragg Gratings*, Academic Press, 1999. The optical fibers 202 with integral bandpass filters 206 may be used in place of optical fibers 110 and filter assembly 106, and may be used in combination with any of the spatial encoding devices described previously to perform the encoding. For example, the optical fibers 202 with integral bandpass filters 206 may be used in combination with the mask encoder 152 described with.reference to FIG. 6.

Figure 11:
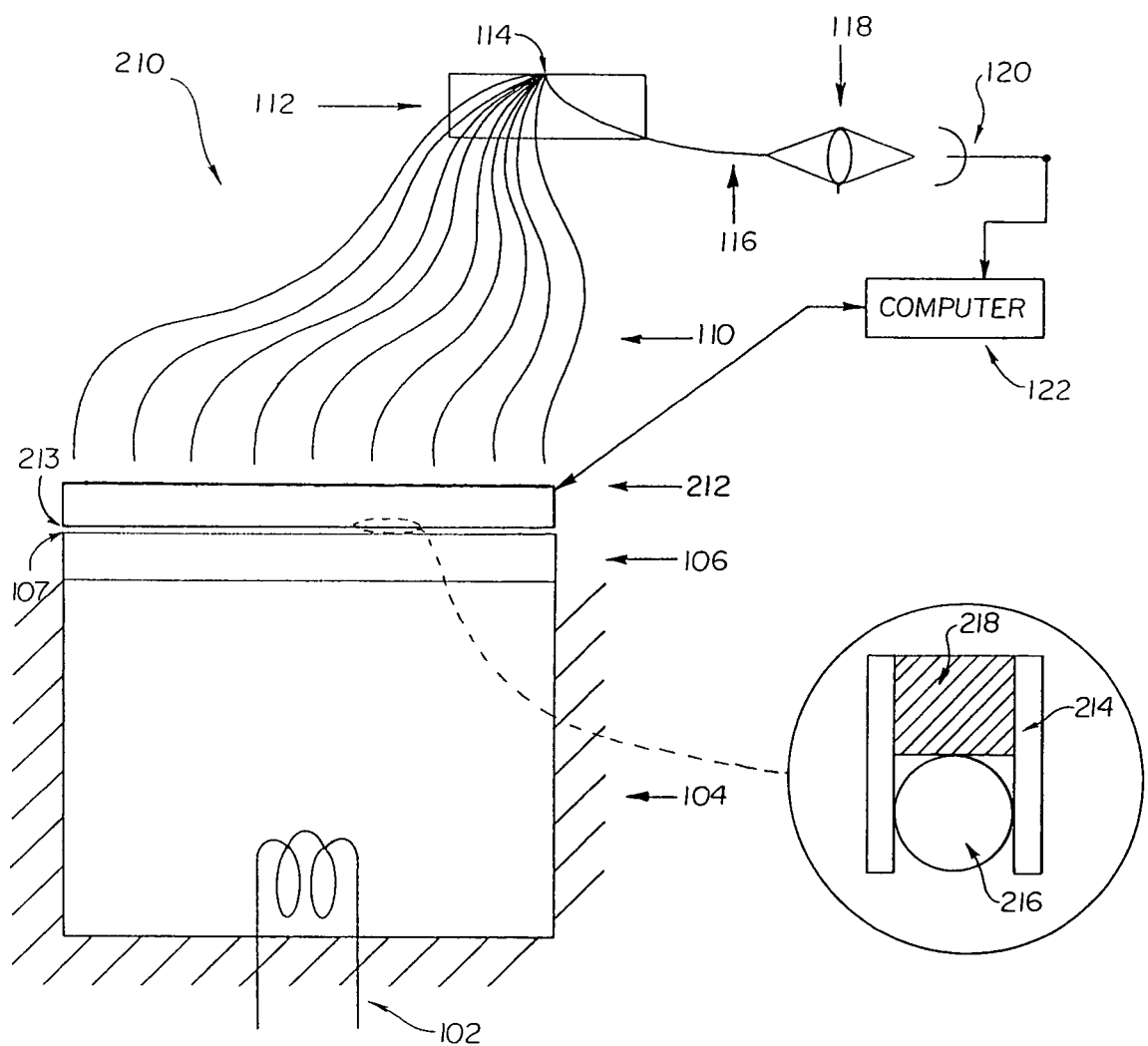
FIG. 11 is a schematic illustration of a spectrometer system utilizing a micro-electromechanical system (MEMS) encoding system in accordance with an embodiment of the present invention.

Refer now to FIG. 11, which is a schematic illustration of a spectrometer system 210 utilizing a micro-electromechanical systems (MEMS) encoding system 212. The leading or bottom surface 213 of the MEMS device 212 is placed in intimate contact with the active or top layer 107 of the filter 106. Alternatively, a lens or a lens array may be used to optically connect the filter 106 to the MEMS device 212. The individual elements of the MEMS device 212 may be controlled by the computer 122 to affect the optical encoding. Each of the MEMS devices 212 include an aperture 216 and optically opaque sliding door or cover 218 supported by members 214 to selectively open and close aperture 216. The apertures are preferably 10–1000 microns in size or diameter. As known in the art, the sliding geometry is one of many ways that multiple optical apertures can be implemented in a MEMS device.

Figure 12:
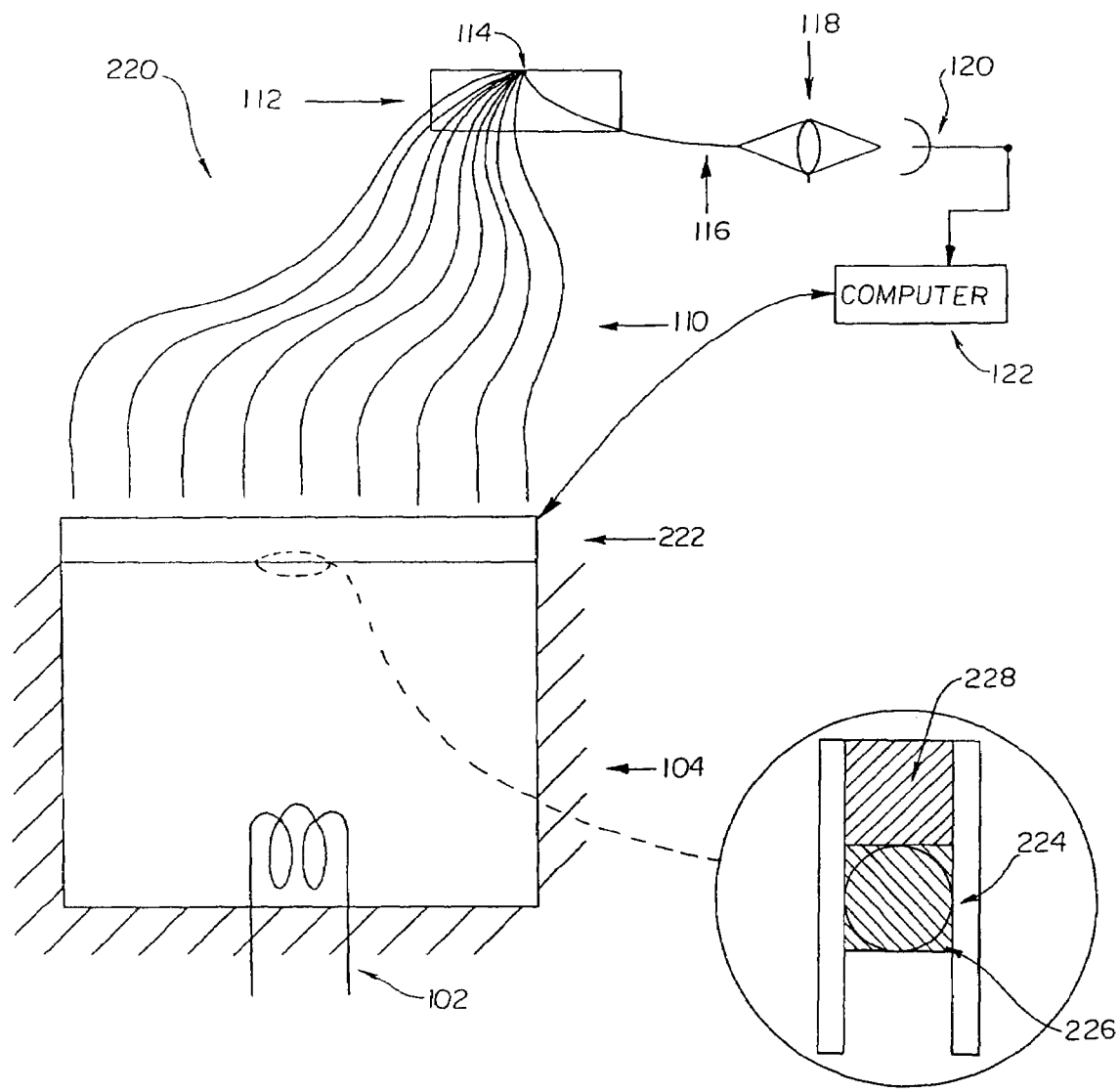
FIG. 12 is a schematic illustration of a spectrometer system utilizing a MEMS-based spectral encoding unit in accordance with an embodiment of the present invention.

Refer now to FIG. 12, which is a schematic illustration of a spectrometer system 220 utilizing a combined filter and MEMS-based spectral encoding unit 222. Generally speaking, the filter 106 and the MEMS aperture can be combined to produce a single spectral encoding unit 222. Other aspects are substantially the same as described with reference to MEMS device 212 illustrated in FIG. 11. Each of the MEMS elements either blocks light or performs optical bandpass filtering. A very small dielectric filter 226 covers the MEMS aperture which, is then selectively opened and closed by door or cover 228 as supported by members 224. These apertures are preferably about 10–1000 microns in size or diameter.

Figure 13:
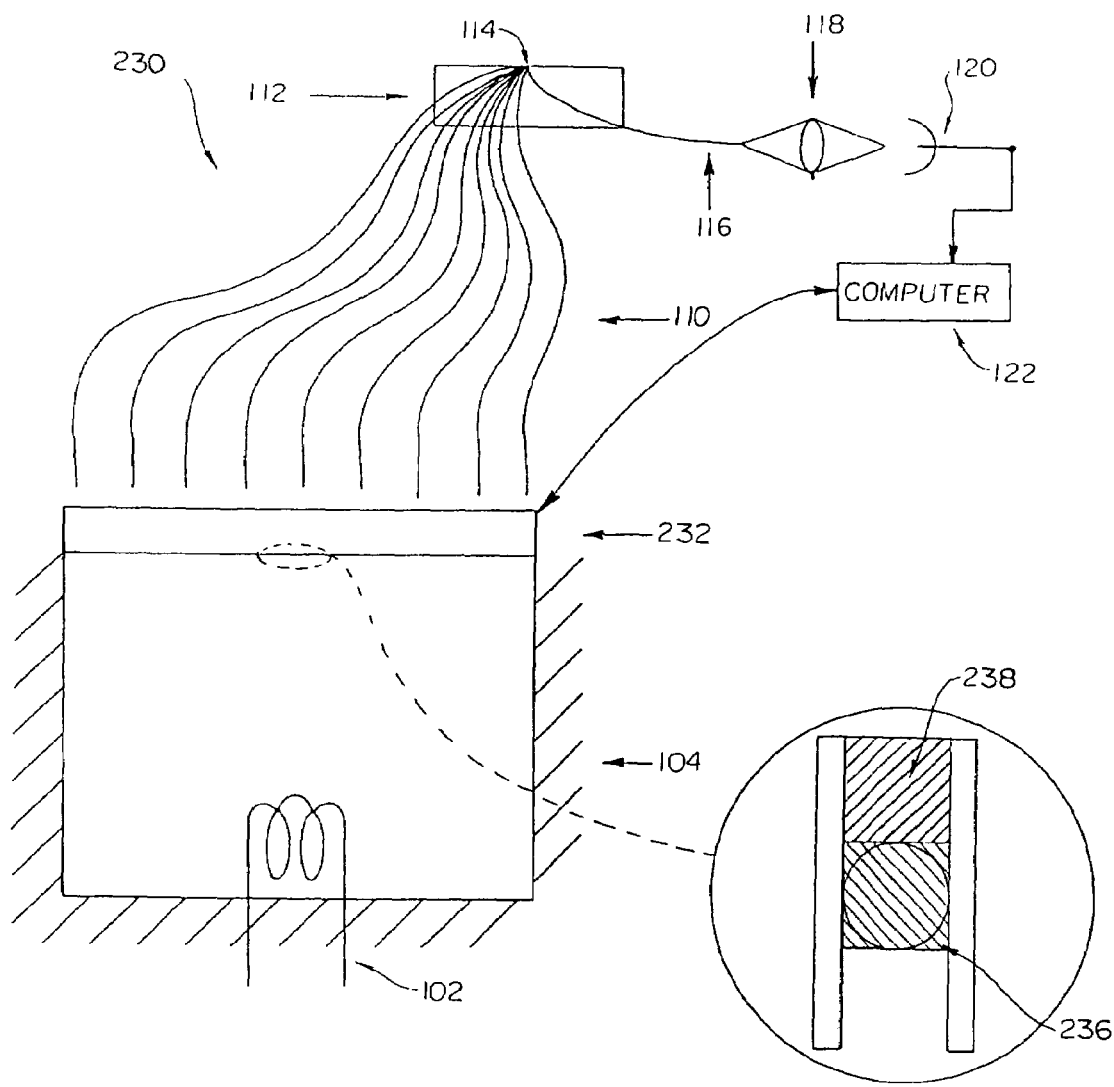
FIG. 13 is a schematic illustration of a spectrometer system utilizing a MEMS-based double encoding system in accordance with an embodiment of the present invention.

Refer now to FIG. 13, which is a schematic illustration of a spectrometer system 230 utilizing a MEMS double encoding system 232. Basically, the MEMS double encoding system 232 comprises the MEMS encoding unit 222 described with reference to FIG. 12, but incorporates two different bandpass filters 236/238 in each encoding element, rather than an open/closed door or cover. In this way, all of the wavelengths may be addressed using half of the elements as necessary with the MEMS encoding unit 222 described with reference to FIG. 12. In general, the MEMS double encoding system 232 provides a signal that is different than a Hadamard transform, but can still be practically applied to some types of analyte measurements. A simulation of the double encoding apparatus and method of FIG. 13 has been generated. The data set used was a set of forearm tissue spectra that were collected on forty (40) diabetic subjects. The subjects were roughly evenly divided between Type I and Type II diabetes, were evenly divided between males and females, spanned ages from 23 years old to 67 years old, and had an ethnic composition that approximated the local population. Each subject who participated in the study was measured during two sessions per week for a total of seven weeks. Each subject had a number of capillary blood draws taken per visit, which were used in conjunction with a Yellow Springs analyzer to determine a blood glucose reference value. As well, during each visit, the subjects had four 90-second optical samples taken of their forearms using a system based upon a Bomem WorkIR FTIR spectrometer operating at a spectral resolution of 16 $cm^{-1}$.

The resulting FTIR data were processed in the usual way to produce 1874 intensity spectra that had significant detected intensity in the range from 4200 to 7200 $cm^{-1}$ and were approximately zero elsewhere. Standard outlier techniques based upon the spectral Mahalanobis distance and the spectral F-ratio as described by Haaland, *Computer Enhanced Analytical Spectroscopy*, Volume 3, Plenum Press, 1992, were applied to these data to remove outliers (127 spectra) from the data set. The resulting spectral data and their corresponding blood glucose reference values were then used to simulate the double encoding method and other related techniques.

The original intensity spectra were encoded in two ways: First, they were encoded using a simulation of a conventional Hadamard S-matrix encoding scheme using a 383× 383 element transformation matrix. Second, they were encoded using a simulation of a double encoding scheme using the following procedure: the intensity spectra were trimmed slightly to 382 pixels (from 391 originally). Then a 192×192-element Hadamard matrix was generated using the Hadamard Matlab function. This was then converted to an S-matrix by methods well known to one knowledgeable in the art. The resulting 191×191 element S-matrix was then doubled by replacing each entry that was [0] by [1 0] and each [1] entry by [0 1]. The resulting 382×382 matrix was then mapped randomly to spectral elements and then applied to the spectra. This procedure simulated a double encoding mask with random pairings of filters at each aperture.

The resulting spectral data and glucose reference values were mean-centered by patient using the method disclosed in U.S. Pat. No. 6,157,041, entitled "Methods and Apparatus for Tailoring Spectroscopic Calibration Models", then used to perform a patient-out cross-validation for glucose values. As well, a logarithmic transform was applied to these same data, followed by a noise-scaling function that was proportional to intensity at each element, which were also mean-centered by subject and used for a subject-out cross-validation. As a comparison, the conventional S-matrix simulation data were used for cross-validation, as were data based on the original spectral intensity values. In all of these cases, the corresponding log-scaled data were also generated and used for cross-validation.

As shown in Table 1, the simulations indicated that the scaled-log of the original intensity spectra (i.e., noise scaled absorbance) produced the best result of approximately 23.3 mg/dl standard error of prediction (SEP) for glucose. Next in performance, the scale-log of the S-matrix data and the double-encoded data resulted in an SEP of approximately 25.7 mg/dl in both cases. Finally, the raw spectral data, the raw S-matrix data and the raw double-encoded data all produced results of approximately 27.5 mg/dl. The differences between the different data treatments that were studied were small. This similarity of results indicates that the direct use of double encoded data or the scaled-log transformation of the double encoded data is a viable option that could provide a less expensive encoding unit 232 as well as reduced computational requirements for the spectrometer system computer 122.

TABLE 1

Results of Encoding Simulations

| | SEP [mg/dl]: Raw Data | SEP [mg/dl]: Scaled-Logarithm of the Data |
|---|---|---|
| Original Spectral Data | 27.5 | 23.3 |
| S-Matrix Simulation Data | 27.5 | 25.7 |
| Double-Encoded Simulation Data | 27.5 | 25.7 |

Figure 14:
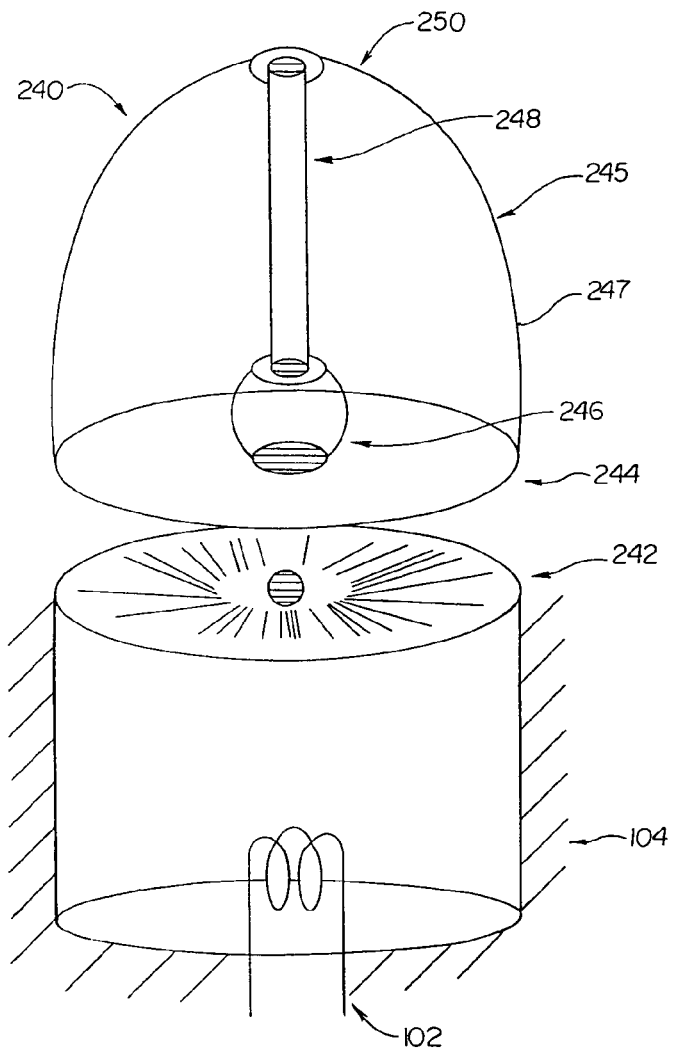
FIG. 14 is a schematic illustration of a spectrometer system utilizing an integrated non-fiber arrangement in accordance with an embodiment of the present invention.

All of the spectrometer systems described thus far utilize optical fibers in one context or another. However, those skilled in the art will recognize that the spectrometer systems of the present invention may also be used without optical fibers. For example, refer now to FIG. 14, which is a schematic illustration of a spectrometer system 240 utilizing an integrated non-fiber design. Spectrometer system 240 includes an encoding unit 242 such as a rotary mask type encoder 152 described with reference to FIG. 6. Spectrometer system 240 also includes a filter 244 such as a stationary circular variable filter (CVF) that is similar to the rotating CVF device 162 described with reference to FIG. 7. The encoding unit 242 and filter 244 may comprise any of the encoder/filter combinations described previously.

All the light leaving the encoding unit 242 and filter 244 enters into a non-imaging optical concentrator 245 that directs the light to illuminate the tissue at the sample head 250. The optical concentrator 245 comprises a dome 247 having a reflective inner surface to direct and focus the filtered light on the sample head 250. An optical light pipe 248 or other equivalent device is then used to capture the diffusely reflected light and direct it into an appropriate single-element detector 246, which can be located inside of the concentrator 245, as shown in the figure, or can be placed in a convenient position outside the concentrator, if desired, by having light pipe 248 pass through the dome 247 at some point. The detector 246 is coupled to the computer 122 as in prior embodiments. Those skilled in the art will recognize that the non-fiber concepts described with reference to spectrometer system 240 may be incorporated into any of the spectrometer systems described herein. The non-fiber spectrometer system 240 described above, in addition to other non-fiber embodiments contemplated herein, offer advantages in the terms of cost, ruggedness and/or ease of assembly.

Figure 15:
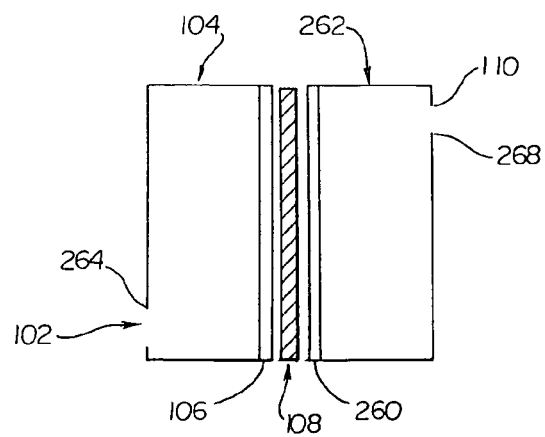
FIG. 15 is a schematic illustration of a spectrometer system utilizing an input integrating chamber and linear variable filter passing light to a spatial encoder with light exiting the encoder and striking a second linear variable filter and integrating chamber to allow for a smaller area collection bundle or detector.

Referring now to FIG. 15, an alternative dual-chamber linear variable filter spectrometer is schematically depicted. The spectrometer system depicted in FIG. 15 shows an alternative to design to the basic linear variable filter (LVF) or circular variable filter (CVF) spectrometers previously described. With the basic LVF spectrometer design, the output of the LVF is distributed spatially over a relatively large area. Adding a second LVF, in the arrangement shown, allows the light from the large LVF surface area to be efficiently collected into a smaller exit port. As with previous embodiments using the LVF and integrating chamber, it is assumed that for monochromatic light the LVF surface is highly reflective, except in the area representing the passband region for the particular wavelength of the monochromatic light.

Light from the source 102 to be analyzed goes through an entrance port 264 into the first integrating chamber 104, consisting of highly reflective walls. The front wall is of planar geometry and contains a first LVF 106. The back wall, containing the entrance port, is also planar and parallel to the front wall. The side walls may be planar, as with a polygon cross-section, or curved, as with a cylinder. Light of a specific wavelength (monochromatic) within the passband of the LVF 106, upon entering the chamber, will be reflected between the walls of the chamber until it strikes the appropriate passband region of the LVF 106 to be admitted through. Similarly, light of other wavelengths within the LVF 106 passband pass through the LVF 106 at different positions corresponding to their wavelength. Light passing through the LVF 106 is then spatially encoded by the spatial encoding device 108 and allowed to pass through a second LVF 260 with the spatial distribution of wavelength passbands matching those of the first LVF 106. This second LVF 260 is on one face of a second integrating chamber 262, similar to the first integrating chamber 104. Light passing through the second LVF 260 will reflect between the walls until a portion of it reaches the exit port 268 contained in the wall opposite the second LVF 260. The next stage can be either a single detector element or a relay system (e.g., fiber optics) to transmit the light to a tissue sampler. The integrating chambers, as described here preserve the numerical aperture (NA) of the light entering the chamber. Appropriate optics can then be added to adjust the NA before entering the input chamber and after leaving the output chamber to optimize the system for each of the components. The integrating chambers used herein may consist of a hollow chamber with reflective internal walls or of a solid block of transparent refracting material with the reflective and wavelength selective surfaces deposited on the outside walls so as to enhance and control the internal reflections.

To understand the advantage of the second LVF/integrating chamber requires defining a few quantities. Let, Alvf=total area of the face of the linear variable filter N=number of wavelength passbands contained within Alvf, i.e. the number of spectral resolution elements of the spectrometer Ae=exit port area for a system not containing the second LVF/integrating chamber the total area over which light must be collected is equal to Alvf. This area could represent the area of a detector used to collect the signal, or it could represent the area of a fiber optic bundle used to collect the light to transport it to a sampler. For many applications, the need to collect the light over a large area is a disadvantage. For example, the cost of a detector or the noise generated by a detector is often proportional to the detector surface area. Likewise, a large area fiber optic bundle is more costly than a small area fiber bundle.

The second LVF/integrating chamber affords a means of reducing this collection area to Ae, which can be much smaller than Alvf. To look at the efficiency of light transfer, we need to recognize that there are three ways a monochromatic ray of light can escape from the second chamber. First, it can go back through the LVF in the small area equal to Alvf/N, representing the surface area occupied by the passband region of the LVF corresponding to the wavelength of the monochromatic ray; second, it can be absorbed in the reflective walls of the integrating chamber or in the propagation medium of the chamber; or third, it can go out the exit port area Ae. If we ignore the losses due to absorption, the portion going through the exit port is equal to Ae/(Ae+Alvf/N). As a single example, using this equation, we see that if we make the exit port area, Ae, equal to Alvf/N, we will collect 50% of the light entering the second chamber. In many cases, this 50% loss would be greatly preferred over having to make a detector or fiber optic bundle N times larger in area.

From the foregoing, it should be apparent to those skilled in the art that the present invention provides a number of spectroscopic systems and spectrometers that utilize an encoder and a bandpass filter to produce a single-element multiplexing spectrometer. The use of an integrating chamber further increases the SNR and system performance when it is incorporated into the system in such a way that light outside the bandpass region of the optical filter is reflected back into the integrating chamber where it is retransmitted to the filter, resulting in a significant increase in the optical power passing through the filter. The integrating chamber essentially boosts the optical throughput of the spectroscopic system and increases the signal-to-noise ratio of the system. The integrating chamber allows direct illumination of the filter from the light source and also allows the light reflected back from the filter to make additional attempts to pass through the filter. The integrating chamber maximizes the return of the reflected light to the filter assembly and minimizes optical losses.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A spectrometer system for performing spectroscopic determination on biological media, the spectrometer system comprising:

a light source for generating light;

an optical filter positioned to receive light from the light source, the filter having a plurality of bandpass regions, wherein light within a bandpass region is transmitted through the filter such that for each bandpass region there is a corresponding pasaband of light;

an optical encoding unit positioned for encoding selected passbands of light corresponding to bandpass regions of the optical filter, the optical encoding unit configured for selecting subsets of the passbands of light;

a sampler for transmitting the light into the sample and for receiving the non-absorbed light from the sample; and a detector for receiving the non-absorbed light and for generating an electric signal indicative of the non-absorbed light;

wherein the sampler is configured to receive the filtered, encoded light from the encoder.

2. A spectrometer system as in claim 1, wherein the optical filter substantially reflects light when the incident light is of a wavelength outside the plurality of bandpass regions.

3. A spectrometer system 25 in claim 2, further comprising an optical integrating chamber wherein light reflected from the optical filter is substantially directed into the chamber and then refleaed back to the optical filter.

4. A spectrometer system as in claim 3, wherein the spectrometer system has a signal-to-noise ratio, and wherein the integrating chamber increases the signal-to-noise ratio.

5. A spectrometer system as in claim 4, wherein the integrating chamber allows direct illumination of the filter from the light source.

6. A spectrometer system as in claim 5, wherein the integrating chamber is an orthogonal design to preserve angular qualities of the light entering the integrating chamber.

7. A spectrometer system as in claim 3, wherein the light source is disposed inside the integrating chamber.

8. A spectrometer system as in claim 3, wherein the light source is disposed outside the integrating chamber.

9. A spectrometer system as in claim 1, wherein the sampler is disposed adjacent the detector.

10. A spectrometer system as in claim 1, wherein the sampler is disposed adjacent the light source.

11. A spectrometer system as in claim 1, wherein the optical filter is disposed adjacent the light source.

12. A spectrometer system as in claim 1, wherein the optical encoding unit is disposed adjacent the light source.

13. A spectrometer system as in claim 1, wherein the optical filter comprises one or more dielectric bandpass fllters.

14. A spectrometer system as in claim 13, wherein the optical filter comprises a linear variable filter.

15. A spectrometer system as in claim 13, wherein the optical filter comprises a non-linear variable filter.

16. A spectrometer system as in claim 1, wherein the optical filter comprises a plurality of individual bandpass filters.

17. A spectrometer system as in claim 1, wherein the optical bandpass filters are embodied in optical fibers.

18. A spectrometer system as in claim 1, wherein the optical filter comprises a circular variable filter.

19. A spectrometer system as in claim 1, wherein the encoding unit comprises a spatial light modulator.

20. A spectrometer system as in claim 19, wherein the encoding unit comprises a rotary mask having an aperture array.

21. A spectrometer system as in claim 19, wherein the encoding unit comprises a linear translation mask having an aperture array.

22. A spectrometer system as in claim 19, wherein the encoding unit comprises a liquid crystal spatial light modulator.

23. A spectrometer system as in claim 19, wherein the encoding unit comprises a micro-electromechanical system.

24. A spectrometer system as in claim 23, wherein the individual micro-apertures are controllable to be either substantially transmissive or opaque.

25. A spectrometer system as in claim 23, wherein the individual micro-apertures are controllable to be either an optical bandpass filter or opaque.

26. A spectrometer system as in claim 23, wherein the individual micro-apertures are controllable to be one of a plurality of optical bandpass filters.

27. A spectrometer system as in claim 1, wherein the encoding unit comprises a digital mirror device.

28. A spectrometer system as in claim 1, wherein the optical filter and the encoding unit are combined into a single unit.

29. A spectrometer for use in a spectroscopic system, the spectroscopiC system including a light source for generating light and a detector for receiving light, the spectrometer comprising:

an optical filter for receiving light from the light source, the filter having a plurality of bandpass regions, wherein light within a handpass region is transmitted through the optical filter such tat for each bandpass region there is a corresponding passband of light, the optical filter further disposed such that a plurality of passbands of light pass through the optical filter from the light source simultaneously; and an encoding unit for encoding selected passbands of light corresponding to bandpass regions of the optical fdter, the optical encoding unit configured for selecting subsets of the passbands of light;

wherein the encoding unit is operable to select at least a first subset of the passbands of light or a second sabser of the passbands of light for transmission to a sampler adapted to interrogate a biologaical sample.

30. A spectrometer as in claim 29, wherein the optical filter substantially reflects light when the incident light is of a wavelength outside the plurality of bandpass regions.

31. A spectrometer as in claim 30, farther comprising an optical integrating chamber wherein light reflected from the optical filter is substantially directed into the chamber and then reflected back to the optical filter.

32. A spectrometer as in claim 31, wherein the spectrometer has a signal-to-noise ratio, and wherein the integrating chamber increases the signal-to-noise ratio.

33. A spectrometer as in claim 32, wherein the integrating chamber allows direct illumination of the filter from the light source.

34. A spectrometer as in claim 33, wherein the integrating chamber is an orthogonal design to preserve angular qualities of the light entering the integrating chamber.

35. A spectrometer as in claim 29, wherein the optical filter is disposed adjacent the light source.

36. A spectrometer system as in claim 29, wherein the optical encoding unit is disposed adjacent the light source.

37. A spectrometer as in claim 29, wherein the optical filter comprises one or more dielectric bandpass filters.

38. A spectrometer as in claim 37, wherein the optical filter comprises a linear variable filter.

39. A spectrometer as in claim 37, wherena the optical filter comprises a non-linear variable filter.

40. A spectrometer as in claim 37, wherein the optical filter comprises a plurality of individual bandpass filters.

41. A spectrometer as m claim 40, wherein the bandpass optical filters are embodied in optical fibers.

42. A spectrometer as in claim 37, wherein the optical filter comprises a circular variable filter.

43. A spectrometer as in claim 29, wherein the encoding unit comprises a spatial light modulator.

44. A spectrometer as in claim 43, wherein the encoding unit comprises a rotary mask having an aperture array.

45. A spectrometer as in claim 43, wherein the encoding unit comprises a liner translation mask having an aperture array.

46. A spectrometer as in claim 43, wherein the encoding unit comprises a liquid crystal spatial light modulator.

47. A spectrometer as in claim 43, wherein the encoding unit comprises a micro-electromechanical system.

48. A spectrometer as in claim 47, wherein the individual micro-apertures are controllable to be either substantially transmissive or opaque.

49. A spectrometer as in claim 47, wherein the individual micro-apertures are controllable to be either an optical bandpass filter or opaque.

50. A spectrometer as in claim 47, wherein the individual micro-apertures are controllable to be one of a plurality of optical bandpass filters.

51. A spectrometer as in claim 29, wherein the encoding unit comprises a digital mirror device.

52. A spectrometer as in claim 29, wherein the optical filter and the encoding unit are combined into a single unit.

53. A spectrometer for use in selected applications of a spectroscopic system, the spectroscopic system including a light source for generating light and a detector for receiving light, the spectrometer comprising:

an optical filter for receiving light from the tight source, the filter having a plurality of bandpass regions, wherein light within a bandpass region is transmitted through the optical filter such that for each bandpass region there is a corresponding passband of light, the optical filter father disposed such tat a plurality of passbands of light pass through the optical filter from the light source simultaneously, wherein said regions are sized from final regression coefficients derived from said selected application; and an encoding unit for encoding selected pasahands of light corresponding to bandpass region of the optical filter, the optical encoding unit configured for selecting subsets of the passbands of light.

* * * * *

UNITED STATES PATENT AND TRADEMARK OFFICE
CERTIFICATE OF CORRECTION

PATENT NO. : 7,126,682 B2
APPLICATION NO. : 09/832631
DATED : October 24, 2006
INVENTOR(S) : Robert K. Rowe et al.

It is certified that error appears in the above-identified patent and that said Letters Patent is hereby corrected as shown below:

Column 16
Line 67, delete "pasaband" and insert therefor -- passband --.

Column 17
Line 16, delete "25" and insert therefor -- as --.
Line 19, delete "refleaed" and insert therefor -- reflected --.
Line 45, delete "fllters" and insert therefor -- filters --.

Column 18
Line 18, delete "spectroscopiC" and insert therefor -- spectroscopic --.
Line 23, delete "handpass" and insert therefor -- bandpass --.
Line 24, delete "tat" and insert therefor -- that --.
Line 30, delete "fdter" and insert therefor -- filter --.
Line 34, delete "sabser" and insert therefor -- subset --.
Line 36, delete "biologaical" and insert therefor -- biological --.
Line 40, delete "farther" and insert therefor -- further --.
Line 62, delete "wherena" and insert therefor -- wherein --.
Line 66, delete "as m claim 40" and insert therefor -- as in claim 40 --.

Column 19
Line 8, delete "liner" and insert therefor -- linear --.

Column 20
Line 8, delete "tight" and insert therefor -- light --.
Line 13, delete "father disposed such tat" and insert therefor -- further disposed such that --.

UNITED STATES PATENT AND TRADEMARK OFFICE
CERTIFICATE OF CORRECTION

PATENT NO. : 7,126,682 B2
APPLICATION NO. : 09/832631
DATED : October 24, 2006
INVENTOR(S) : Robert K. Rowe et al.

It is certified that error appears in the above-identified patent and that said Letters Patent is hereby corrected as shown below:

Line 18, delete "pasahands" and insert therefor -- passbands --.

Signed and Sealed this

Twentieth Day of February, 2007

JON W. DUDAS
*Director of the United States Patent and Trademark Office*